(12) United States Patent
Lee et al.

(10) Patent No.: US 10,686,145 B2
(45) Date of Patent: Jun. 16, 2020

(54) ORGANIC COMPOUND, ORGANIC THIN FILM, AND ELECTRONIC DEVICE

(71) Applicant: Samsung Electronics Co., Ltd., Suwon-si, Gyeonggi-do (KR)

(72) Inventors: Eun Kyung Lee, Seoul (KR); Jeong Il Park, Seongnam-si (KR); Don-Wook Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/047,208

(22) Filed: Jul. 27, 2018

(65) Prior Publication Data

US 2019/0036037 A1    Jan. 31, 2019

(30) Foreign Application Priority Data

Jul. 28, 2017  (KR) .................. 10-2017-0096200
Feb. 5, 2018   (KR) .................. 10-2018-0013885

(51) Int. Cl.
*C07D 495/22*    (2006.01)
*H01L 51/00*     (2006.01)
*C09B 57/00*     (2006.01)
*C07D 517/22*    (2006.01)
*H01L 51/05*     (2006.01)

(52) U.S. Cl.
CPC ........ *H01L 51/0074* (2013.01); *C07D 495/22* (2013.01); *C07D 517/22* (2013.01); *C09B 57/00* (2013.01); *H01L 51/0071* (2013.01); *H01L 51/0545* (2013.01); *H01L 51/0558* (2013.01); *H01L 51/0566* (2013.01)

(58) Field of Classification Search
CPC ............. H01L 51/0074; H01L 51/0566; H01L 51/0545; C07D 517/22; C07D 495/22; C09B 57/00
USPC ..................................... 549/41, 50
See application file for complete search history.

(56) References Cited

U.S. PATENT DOCUMENTS

| 7,816,673 | B2 | 10/2010 | Park et al. |
| 8,232,546 | B2 | 7/2012 | Takimiya et al. |
| 8,367,717 | B2 | 2/2013 | Kastler et al. |
| 8,816,100 | B2 | 8/2014 | Takimiya |

(Continued)

FOREIGN PATENT DOCUMENTS

| CN | 101200471 A | 6/2008 |
| CN | 101528753 A | 9/2009 |

(Continued)

OTHER PUBLICATIONS

Extended European Search Report dated Nov. 28, 2018 for EP 18185978.6.

(Continued)

*Primary Examiner* — Taylor V Oh
(74) *Attorney, Agent, or Firm* — Harness, Dickey & Pierce, P.L.C.

(57) ABSTRACT

Disclosed are an organic compound selected from a compound represented by Chemical Formula 1A, a compound represented by Chemical Formula 1B, and a combination thereof, an organic thin film including the organic compound, an organic thin film transistor, and an electronic device. The organic compound has liquid crystal properties and exhibits an ordered liquid crystal phase when being heated in a liquid crystal period due to asymmetric substituents and thereby charge mobility may be further improved.

22 Claims, 12 Drawing Sheets

(56) References Cited

U.S. PATENT DOCUMENTS

| | | | |
|---|---|---|---|
| 9,954,183 | B2 | 4/2018 | Miyazaki et al. |
| 2008/0142792 | A1 | 6/2008 | Park et al. |
| 2009/0043113 | A1 | 2/2009 | Park et al. |
| 2009/0261300 | A1 | 10/2009 | Watanabe |
| 2010/0065826 | A1 | 3/2010 | Takimiya et al. |
| 2011/0224445 | A1 | 9/2011 | Takimiya |
| 2013/0116447 | A1 | 5/2013 | Park et al. |
| 2013/0163570 | A1 | 6/2013 | Zhang et al. |
| 2013/0277657 | A1 | 10/2013 | Park et al. |
| 2013/0320316 | A1 | 12/2013 | Park et al. |
| 2016/0226005 | A1 | 8/2016 | Park et al. |
| 2016/0372686 | A1 | 12/2016 | Hahm et al. |
| 2017/0098786 | A1 | 4/2017 | Kitamura et al. |
| 2017/0317296 | A1 | 11/2017 | Yamamoto et al. |

FOREIGN PATENT DOCUMENTS

| | | | |
|---|---|---|---|
| CN | 103467489 | A | 12/2013 |
| EP | 1932847 | A1 | 6/2008 |
| EP | 2067782 | A1 | 6/2009 |
| EP | 2098527 | A1 | 9/2009 |
| EP | 2671880 | A1 | 12/2013 |
| EP | 3 050 887 | A1 | 8/2016 |
| JP | 2010-150229 | | 7/2010 |
| JP | 2010-177643 | A | 8/2010 |
| JP | 2010-254599 | | 11/2010 |
| JP | 2011-526588 | | 10/2011 |
| JP | 4958119 | | 6/2012 |
| JP | 2015-170758 | | 9/2015 |
| JP | 2017034247 | A | 2/2017 |
| KR | 10-2008-0054553 | | 6/2008 |
| KR | 20080100982 | A | 11/2008 |
| KR | 10-2013-0050266 | | 5/2013 |
| KR | 2013-0050266 | A | 5/2013 |
| KR | 2013-0064776 | A | 6/2013 |
| KR | 20130118629 | A | 10/2013 |
| KR | 20130136938 | A | 12/2013 |
| KR | 10-2016-0093550 | | 8/2016 |
| WO | WO-2008-050726 | A1 | 5/2008 |
| WO | WO-2009/009790 | A1 | 1/2009 |
| WO | WO-2009/0009790 | A1 | 1/2009 |
| WO | WO-2016/148170 | | 9/2016 |

OTHER PUBLICATIONS

Extended European Search Report dated Jun. 16, 2016 issued in corresponding European Patent Application No. 16152968.0.
Chinese Office Action dated Jan. 29, 2018 issued in corresponding Chinese Application No. 201610064600.3 (English translation provided).
Notice of Allowance and Fee(s) Due dated Jan. 17, 2019 for co-pending U.S. Appl. No. 15/008,976.
Final Office Action for co-pending U.S. Appl. No. 15/008,976 dated Sep. 21, 2018.
Extended European Search Report dated Apr. 1, 2019, issued in corresponding European Patent Application No. 18185978.6.
Hiroaki Lino et al., "Liquid crystals for organic thin-film transistors", Nature Communications 6:6828, Apr. 10, 2015.
U.S. Notice of Allowance dated Oct. 10, 2019 issued in co-pending U.S. Appl. No. 15/008,976.

ORGANIC COMPOUND, ORGANIC THIN FILM, AND ELECTRONIC DEVICE

CROSS-REFERENCE TO RELATED APPLICATION

This application claims priority to and the benefit of Korean Patent Application Nos. 10-2017-0096200 and 10-2018-0013885, filed in the Korean Intellectual Property Office on Jul. 28, 2017 and Feb. 5, 2018, respectively, the entire contents of which are incorporated herein by reference.

BACKGROUND

1. Field

An organic compound, an organic thin film, and an electronic device are disclosed.

2. Description of Related Art

A flat panel display such as a liquid crystal display (LCD), an organic light emitting diode (OLED) display, an electrophoretic display, and the like includes a pair of electric field-generating electrodes and an electrical optical active layer interposed therebetween. The liquid crystal display (LCD) includes a liquid crystal layer as an electric optical active layer, and the organic light emitting diode (OLED) display includes an organic emission layer as an electrical optical active layer.

One of the pairs of the electric field-generating electrodes is commonly connected to a switching device and receives an electrical signal, and the electrical optical active layer transforms the electrical signal into an optical signal and thus displays an image.

The flat panel display includes a three-terminal element of a thin film transistor (TFT) as a switch, and it also includes a gate line transferring a scan signal for controlling the thin film transistor and a data line transferring a data signal to be applied to a pixel electrode.

Among the thin film transistors, an organic thin film transistor (OTFT) including an organic semiconductor such as a low molecular compound or a polymer instead of the inorganic semiconductor such as silicon (Si) has been actively researched.

The organic thin film transistor may be made into a fiber or a film due to characteristics of an organic material, and thus is drawing attention as a core element for a flexible display device. The organic thin film transistor may be manufactured using a solution process such as inkjet printing, and may be easily applied to a large area flat panel display where a deposition process has a limit.

SUMMARY

An embodiment provides an organic compound that is applicable to an electronic device such as an organic thin film transistor.

Another embodiment provides an organic thin film including the organic compound.

Yet another embodiment provides an electronic device including the organic thin film.

According to one embodiment, an organic compound is selected from a compound represented by Chemical Formula 1A, a compound represented by Chemical Formula 1B, and a combination thereof.

[Chemical Formula 1A]

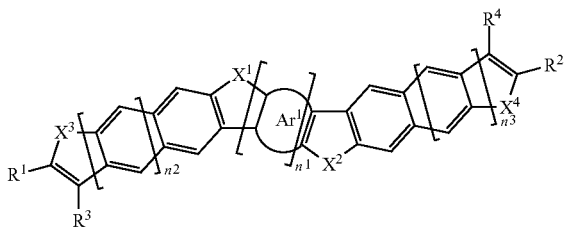

[Chemical Formula 1B]

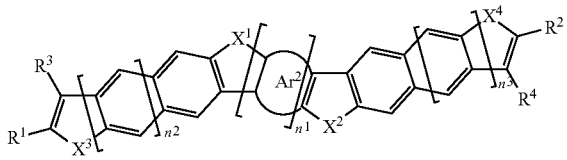

In Chemical Formulae 1A and 1B, $Ar^1$ and $Ar^3$ are independently one of benzene, naphthalene, or anthracene, $X^1$ to $X^4$ are independently one of O, S, Se, Te, or $NR^a$, wherein $R^a$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, n1, n2, and n3 are independently 0 or 1, $R^1$ to $R^4$ are independently one of hydrogen, a halogen atom, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are different structures from each other or $R^3$ and $R^4$ are different structures from each other.

In some embodiments, n1 is 0 and n2=n3, n1 is 1 and n2=n3=0.

In some embodiments, of $R^1$ and $R^2$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, and an other of $R^1$ and $R^2$ may be one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ are independently one of hydrogen or a halogen atom; or one of $R^3$ and $R^4$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, and an other of $R^3$ and $R^4$ may be a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ may independently be one of hydrogen or a halogen atom.

In some embodiments, one of $R^1$ and $R^2$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and an other of $R^1$ and $R^2$ may be one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ may independently be one of hydrogen or a halogen atom; or one of $R^3$ and $R^4$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, an other of $R^3$ and $R^4$ may be one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ may independently be one of hydrogen or a halogen atom.

In some embodiments, in Chemical Formula 1A or 1B, $X^4$ may be S, and $R^2$ may be one of a fluoro-substituted C6 to C30 aryl group, a fluoro-substituted C2 to C30 heteroaryl group, a fluoro-substituted C7 to C30 alkylaryl group, a fluoro-substituted C2 to C30 alkylheteroaryl group, a fluoro-substituted C5 to C30 cycloalkyl group, a fluoro-substituted C2 to C30 heterocycloalkyl group, or a combination thereof.

In some embodiments, in Chemical Formula 1A or 1B, $R^2$ may be one of a substituted or unsubstituted pentagonal ring, a substituted or unsubstituted hexagonal ring, or a combination thereof.

In some embodiments, in Chemical Formula 1A or 1B, $R^2$ may be one of a heterocyclic group represented by Chemical Formula 2A or 2B, a substituted or unsubstituted alkylaryl group represented by Chemical Formula 2C, or a combination thereof.

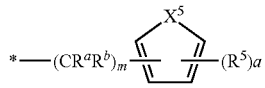
[Chemical Formula 2A]

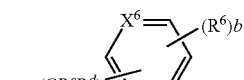
[Chemical Formula 2B]

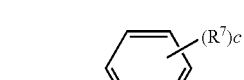
[Chemical Formula 2C]

In Chemical Formulae 2A, 2B, and 2C, $X^5$ is one of O, S, Se, Te, or $NR^{aa}$, wherein $R^{aa}$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, $X^6$ is N, $R^5$ $R^6$ and $R^7$ are independently one of a halogen atom, a hydroxy group, a substituted or unsubstituted C1 to C30 alkyl group, a substituted or unsubstituted C1 to C30 alkoxy group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a combination thereof, a is an integer of 0 to 3, b is an integer of 0 to 4, c is an integer of 0 to 4, $R^a$ and $R^b$ are independently one of hydrogen or a C1 to C6 alkyl group, m is 0 to 20, and when m is 2 or more, —$(CR^aR^b)$— is optionally replaced by one of —O—, —C(=O)—, —OC(=O)O—, or —C(=O)O—, $R^c$ and $R^d$ are independently one of hydrogen or a C1 to C6 alkyl group, n is 0 to 20, and when n is 2 or more, —$(CR^cR^d)$— is optionally replaced by one of —O—, —C(=O)—, —OC(=O)O—, or —C(=O)O—, $R^e$ and $R^f$ are independently one of hydrogen or a C1 to C6 alkyl group, r is 0 to 20, when r is 2 or more, —$(CR^eR^f)$— is optionally replaced by one of —O—, —C(=O)—, —OC(=O)O—, or —C(=O)O—, and

* is a linking point.

In addition, one of $R^1$ and $R^2$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^1$ and $R^2$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^3$ and $R^4$ are independently one of hydrogen or a halogen atom; or one of $R^3$ and $R^4$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^3$ and $R^4$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^1$ and $R^2$ are independently one of hydrogen or a halogen atom.

In some embodiments, n1 may be 1 and $Ar^1$ and $Ar^2$ may be benzene.

In some embodiments, the organic compound may have a molecular weight of about 300 to about 5,000.

In some embodiments, $R^1$ and $R^2$ may have different structures from each other and $R^3$ and $R^4$ may independently be one of hydrogen or a halogen atom. Alternatively, $R^3$ and $R^4$ may have different structures from each other, $R^1$ and $R^2$ may independently be one of hydrogen or a halogen atom.

In some embodiments, the compound may exhibit a smectic phase in a temperature-increasing region of about 300° C. of a differential scanning calorimetry (DSC) analysis.

According to some embodiments, an electronic device including the organic thin film transistor is provided.

In some embodiments, the electronic device may be selected from a solar cell, a liquid crystal display (LCD), an organic light emitting diode device, an electrophoretic device, an organic photoelectric device, and an organic sensor.

According to some embodiments, an electronic device including the organic thin film is provided.

According to an embodiment, an organic semiconductor may include one of a first compound represented by Chemical Formula 1A, a second compound represented by Chemical Formula 1B, or a combination thereof.

[Chemical Formula 1A]

[Chemical Formula 1B]

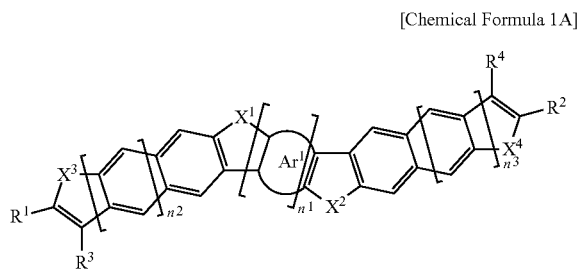

In Chemical Formulae 1A and 1B, $Ar^1$ and $Ar^2$ are independently one of benzene, naphthalene, or anthracene, $X^1$ to $X^4$ are independently one of O, S, Se, Te, or $NR^a$, wherein $R^a$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, n1 is 1, n2 and n3 are 0 or 1, n2=n3, $R^1$ to $R^4$ are independently one of hydrogen, a halogen atom, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are different structures from each other or $R^3$ and $R^4$ are different structures from each other.

In some embodiments, the organic semiconductor may exhibit a smectic phase in a temperature-increasing region of about 300° C. or a different scanning calorimetry (DSC) analysis.

In some embodiments, in Chemical Formula 1A or 1B, $R^2$ may be represented by one of Chemical Formula 2A, Chemical Formula 2B, Chemical Formula 2C, or a combination thereof.

[Chemical Formula 2A]

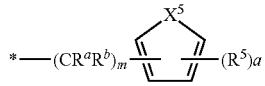

[Chemical Formula 2B]

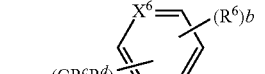

[Chemical Formula 2C]

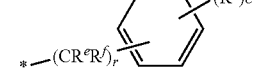

In, Chemical Formulae 2A, 2B, and 2C, $X^5$ is one of O, S, Se, Te, or $NR^{aa}$, wherein $R^{aa}$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, $X^6$ is N, $R^5$ $R^6$ and $R^7$ are independently one of a halogen atom, a hydroxy group, a substituted or unsubstituted C1 to C30 alkyl group, a substituted or unsubstituted C1 to C30 alkoxy group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a combination thereof, a is an integer of 0 to 3, b is an integer of 0 to 4, c is an integer of 0 to 4, $R^a$ and $R^b$ are independently one of hydrogen or a C1 to C6 alkyl group, m is 0 to 20, and when m is 2 or more, —$(CR^aR^b)$— is optionally replaced by one of —O—, —C(=O)—, —OC(=O)O—, or —C(=O)O—, $R^c$ and $R^d$ are independently one of hydrogen or a C1 to C6 alkyl group, n is 0 to 20, and when n is 2 or more, —$(CR^bR^d)$— is optionally replaced by one of —O—, —C(=O)—, —OC(=O)O—, or —C(=O)O—, $R^e$ and $R^f$ are independently one of hydrogen or a C1 to C6 alkyl group, r is 0 to 20, when r is 2 or more, —$(CR^eR^f)$— is optionally replaced by one of —O—, —C(=O)—, —OC(=O)O—, or —C(=O)O—, and

* is a linking point.

In addition, one of $R^1$ and $R^2$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^1$ and $R^2$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^3$ and $R^4$ are independently one of hydrogen or a halogen atom; or one of $R^3$ and $R^4$ may be one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^3$ and $R^4$ may be one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^1$ and $R^2$ are independently one of hydrogen or a halogen atom.

In some embodiments, an organic thin film transistor may include an organic semiconductor layer including the organic semiconductor, a gate electrode facing the organic semiconductor layer, a gate insulating layer between the organic semiconductor layer and the gate electrode, and a source electrode and a drain electrode spaced apart from each other and spaced apart from the gate electrode. The gate insulating layer may be connected to the gate electrode and the organic semiconductor layer. The source electrode and the drain electrode may be connected to the organic semiconductor layer.

In some embodiments, an electronic device may include the organic thin film transistor and the organic semiconductor layer may be on the gate electrode.

An organic compound having high charge mobility and improved solubility is provided. The organic compound has liquid crystal properties and exhibits an ordered liquid crystal phase when being heated in a liquid crystal period due to asymmetric substituents and thereby charge mobility may be further improved.

DETAILED DESCRIPTION

Figure 1:
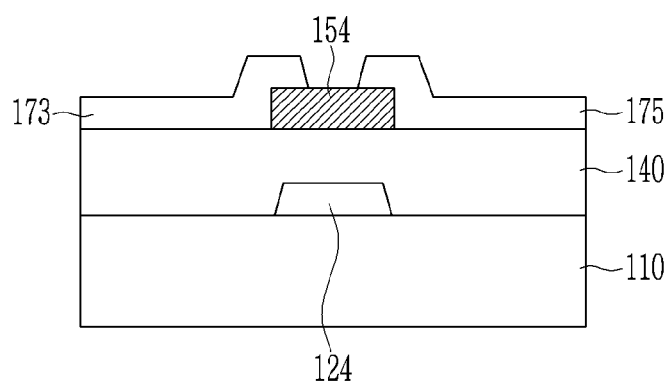
FIG. 1 is a cross-sectional view showing an organic thin film transistor according to an embodiment.

Example embodiments will hereinafter be described in detail, and may be easily performed by a person having an ordinary art in the related art. However, this disclosure may be embodied in many different forms and is not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, "combination thereof" refers to a mixture, a stacked structure, or mutual substitution of constituting components.

As used herein, when a definition is not otherwise provided, "hetero" refers to including 1 to 4 heteroatoms selected from N, O, S, Se, Si, and P in a compound. The total number of ring members may be 3 to 10. If multiple rings are present, each ring is independently aromatic, saturated, or partially unsaturated, and multiple rings, if present, may be fused, pendant, spirocyclic, or a combination thereof. Heterocycloalkyl groups include at least one non-aromatic ring that contains a heteroatom ring member. Heteroaryl groups include at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, when a definition is not otherwise provided, "cyclic group" includes a group not including a heteroatom in a ring and a group including a heteroatom in a ring.

As used herein, when a definition is not otherwise provided, "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, and the like).

"Alkenyl group" refers to a linear or branched saturated monovalent hydrocarbon group including at least one carbon-carbon double bond (e.g., an ethenyl group).

"Alkynyl group" refers to a linear or branched saturated monovalent hydrocarbon group including at least one carbon-carbon triple bond (e.g., ethynyl group).

"Alkoxy group" refers to an alkyl group that is linked via oxygen, e.g., a methoxy, an ethoxy, and a sec-butyloxy group.

"Aryl group" refers to a monovalent functional group formed by the removal of one hydrogen atom from one or more rings of an arene, e.g., phenyl or naphthyl. The arene refers to a hydrocarbon having an aromatic ring, and includes monocyclic and polycyclic hydrocarbons, wherein the additional ring(s) of the polycyclic hydrocarbon may be aromatic or nonaromatic.

"Alkylaryl group" refers to an alkyl group where at least one hydrogen atom is replaced by an aryl group.

"Aryloxy group" refers to an aryl group that is linked via oxygen, and the aryl group is the same as described above.

"Arylalkyl group" refers to an aryl group where at least one hydrogen atom is replaced by a lower alkylene, e.g., methylene, ethylene, propylene, and the like. For example, the "arylalkyl group" may be a benzyl group or a phenylethyl group.

"Cycloalkyl group" refers to a monovalent functional group having one or more saturated rings in which all ring members are carbon, e.g., a cyclopentyl group and a cyclohexyl group.

"Heteroalkyl group" refers to the alkyl group defined above where methylene (—(CH$_2$)—) is replaced by —O—, —S—, —S(=O)$_2$—, —Se—, or —NR— (wherein R is independently hydrogen or a C1 to C10 alkyl group).

"Arylheteroalkyl group" refers to the heteroalkyl group defined above where at least one hydrogen atom is replaced by an aryl group.

"Heteroarylalkyl group" refers to the alkyl group defined above where at least one hydrogen atom is replaced by a heteroaryl group.

"Alkylheteroaryl group" refers to the heteroaryl group defined above where at least one hydrogen atom is replaced by an alkyl group.

As used herein, when a definition is not otherwise provided, "aromatic ring" refers to a functional group in which all atoms in the cyclic functional group have a p-orbital, and wherein these p-orbitals are conjugated. For example, the aromatic ring may be a C6 to C20 aryl group.

As used herein, when a definition is not otherwise provided, the term "substituted" means substitutions with at least one substituent independently selected from a halogen (—F, —Cl, —Br or —I), a C1 to C30 linear or branched alkyl group, for example a C1 to C10 linear or branched alkyl group, a C2 to C30 linear or branched alkenyl group, for example a C2 to C10 linear or branched alkenyl group, a C2 to C30 linear or branched alkynyl group, for example a C2 to C10 linear or branched alkynyl group, a C6 to C30 aryl group, for example a C6 to C12 aryl group, a C2 to C30 heteroaryl group, for example a C2 to C12 heteroaryl group, a C3 to C30 cycloalkyl group, a C1 to C20 fluoroalkyl group, a C1 to C20 perfluoroalkyl group ($C_nF_{2n+1}$), a C1 to C30 linear or branched alkoxy group, a C3 to C30 cycloalkoxy group, a C2 to C30 linear or branched alkoxyalkyl group, a C4 to C30 cycloalkoxyalkyl group, a cyano group, an amino group (—NRR', wherein R and R' are independently hydrogen or a C1 to C10 alkyl group), an amidino group (—C(=NH)NH$_2$), a nitro group (—NO$_2$), an amide group (—C(=O)NHR, wherein R is hydrogen or a C1 to C10 alkyl group), an aldehyde group (—C(=O)H), a hydroxy group (—OH), a sulfonyl group (—S(=O)$_2$R, wherein R is independently hydrogen or a C1 to C10 alkyl group), and a carbamate group (—NHC(=O)OR, wherein R is a C1 to C10 alkyl group), instead of hydrogen of a functional group or a compound, provided that the substituted atom's normal valence is not exceeded.

Hereinafter, an organic compound according to an embodiment is described.

An organic compound according to an embodiment is selected from a compound represented by Chemical Formula 1A, a compound represented by Chemical Formula 1B, and a combination thereof.

[Chemical Formula 1A]

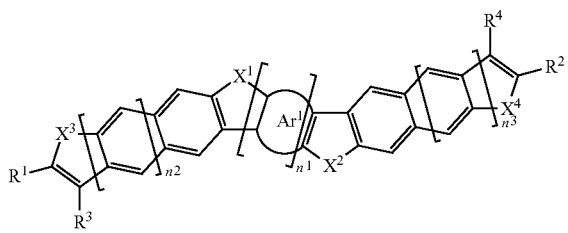

[Chemical Formula 1B]

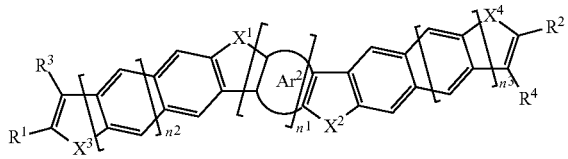

In Chemical Formulae 1A and 1B, $Ar^1$ and $Ar^2$ are independently benzene, naphthalene, or anthracene, $X^1$ to $X^4$ are independently O, S, Se, Te, or $NR^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, n1, n2, and n3 are independently 0 or 1, $R^1$ to $R^4$ are independently hydrogen, a halogen atom, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are groups having a different structure or $R^3$ and $R^4$ are groups having a different structure.

The organic compound is a low molecular compound having two substituents ($R^1$ and $R^2$ or $R^3$ and $R^4$) that are asymmetrically positioned at both terminal ends of a condensed polycyclic group of 6 or more fused rings.

In the present specification "$R^1$ and $R^4$ are groups having a different structure" means that "$R^1$ and $R^2$ are positioned asymmetrically with each other" and "$R^3$ and $R^4$ are groups having a different structure" means that "$R^3$ and $R^4$ are positioned asymmetrically with each other".

The organic compound may increase planarity thereof and packing and stacking between molecules by controlling the number of the fused rings, and may exhibit uniform and stable oxidation potentials due to a compact planar-type molecular structure when the organic compound is applied to an electronic device.

In Chemical Formula 1A or 1B, one fused benzene ring between heterorings is disposed, thereby a molecular interaction is increased due to expansion of a conjugation structure and thus charge mobility and thermal stability may be improved.

In addition, the heterring between benzene rings may improve dissolubility for an organic solvent of the condensed polycyclic heteroaromatic compound.

The organic compound increases a molecular interaction due to a hetero aromatic ring as an outermost ring and thus may have a structure favorable for a molecular arrangement and improved charge mobility.

For example, in Chemical Formula 1A or 1B, when n1 is 0, n2=n3=0 or n2=n3=1, and when n1 is 1, n2=n3=0, but is not limited thereto, and when n1 is 1, $Ar^1$ and $Ar^2$ may be for example benzene. Like this, the organic compound may have controlled properties by controlling the number of fused rings in the core.

The core of the organic compound is a polycyclic cyclic group where at least six pentagonal rings or hexagonal rings, and the organic compound may have improved thermal stability characteristics compared with an organic compound including a core where rings under six are fused, and may be applicable to a deposition or solution process.

The compound may exhibit a smectic phase in a temperature-increasing region of about 300° C. of a differential scanning calorimetry (DSC) analysis.

Hereinafter, $R^1$ to $R^4$ of Chemical Formula 1A and 1B are described.

As described above, the organic compound has two substituents ($R^1$ and $R^2$, or $R^3$ and $R^4$) that are positioned asymmetrically at both terminal ends of the condensed polycyclic group, wherein "positioned asymmetrically" means that $R^1$ and $R^2$ are groups having a different structure or $R^3$ and $R^4$ are groups having a different structure.

Herein, "groups having a different structure" may for example mean the followings (i) to (iv), but is not limited thereto, and if two groups have different structural difference, the two groups are "groups having a different structure":

(i) one of the two includes a linear or branched hydrocarbon moiety and the other includes a cyclic group;

(ii) one of the two includes a branched hydrocarbon moiety and the other includes a cyclic group;

(iii) one of the two includes a branched hydrocarbon moiety and the other includes a linear hydrocarbon moiety; or (iv) one of the two is hydrogen, a halogen atom, or a combination thereof and the other is an aliphatic group, an aromatic group, or a combination thereof.

For example, in Chemical Formula 1A or 1B, one of $R^1$ and $R^2$ may for example be a substituted or unsubstituted linear C1 to C30 alkyl group, a substituted or unsubstituted linear C2 to C30 alkenyl group, a substituted or unsubstituted linear C2 to C30 alkynyl group, or a combination thereof, the other of $R^1$ and $R^2$ may be a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ are independently hydrogen or halogen atom.

For example, one of $R^1$ and $R^2$ may for example be a substituted or unsubstituted branched C3 to C30 alkyl group, a substituted or unsubstituted branched C4 to C30 alkenyl group, a substituted or unsubstituted branched C4 to C30 alkynyl group, or a combination thereof, the other of $R^1$ and $R^2$ may for example be a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ are independently hydrogen or a halogen atom.

For example, one of $R^1$ and $R^2$ may for example be a substituted or unsubstituted linear C1 to C30 alkyl group, a substituted or unsubstituted linear C2 to C30 alkenyl group, a substituted or unsubstituted linear C2 to C30 alkynyl group, or combination thereof, and the other of $R^1$ and $R^2$ may be a substituted or unsubstituted branched C1 to C30 alkyl group, a substituted or unsubstituted branched C2 to C30 alkenyl group, a substituted or unsubstituted branched C2 to C30 alkynyl group, or a combination thereof.

For example, in Chemical Formula 1A or 1B, one of $R^1$ and $R^2$ may for example be hydrogen or a halogen atom, and the other $R^1$ and $R^2$ may be a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof.

As described above, $R^1$ and $R^2$ are for example positioned asymmetrically, but the above descriptions are also applied to the case when $R^3$ and $R^4$ are positioned asymmetrically.

For example, when $R^1$ and $R^2$ are groups having a different structure (i.e., when $R^1$ and $R^2$ are positioned asymmetrically), $R^3$ and $R^4$ may independently be hydrogen or a halogen atom, but are not limited thereto. Likewise, when $R^3$ and $R^4$ are groups having a different structure (i.e., when $R^3$ and $R^4$ are positioned asymmetrically), $R^1$ and $R^2$ may independently be hydrogen or a halogen atom, but are not limited thereto.

For example, in Chemical Formula 1A or 1B, $R^1$ may be a substituted or unsubstituted linear or branched C1 to C30 alkyl group, $R^2$ may be a substituted or unsubstituted C6 to C30 aryl group, and $R^3$ and $R^4$ may independently be hydrogen or a halogen atom, but are not limited thereto.

For example, in Chemical Formula 1A or 1B, $R^3$ may be a substituted or unsubstituted linear or branched C1 to C30 alkyl group, $R^4$ may be a substituted or unsubstituted C6 to C30 aryl group, and $R^1$ and $R^2$ may independently be hydrogen or a halogen atom, but are not limited thereto.

For example, the organic compound may have increased solubility by including for example the aliphatic chain group at one side of the condensed polycyclic group and increased heat resistance by including the cyclic group.

For example, in the organic compound represented by Chemical Formula 1A or 1B, when $R^1$ and $R^2$ are positioned asymmetrically, $X^4$ may be S, and $R^2$ may be a fluoro-substituted C6 to C30 aryl group, a fluoro-substituted C2 to C30 heteroaryl group, a fluoro-substituted C7 to C30 alkylaryl group, a fluoro-substituted C2 to C30 alkylheteroaryl group, a fluoro-substituted C5 to C30 cycloalkyl group, a fluoro-substituted C2 to C30 heterocycloalkyl group, or a combination thereof. In this case, interaction between S of the thiophene moiety of the core and F of the substituent may be reinforced.

For example, the organic compound represented by Chemical Formula 1A or 1B, when $R^1$ and $R^2$ are asymmetric, $R^2$ may be for example a substituted or unsubstituted pentagonal ring, a substituted or unsubstituted hexagonal ring, or a combination thereof, and specifically $R^2$ may be for example a heterocyclic group represented by Chemical Formula 2A or 2B, a substituted or unsubstituted alkylaryl group represented by Chemical Formula 2C, or a combination thereof, but is not limited thereto. Herein, the "combination" refers to fusion of two or more cyclic groups.

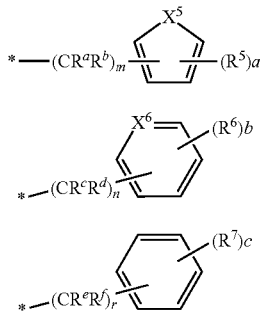

[Chemical Formula 2A]

[Chemical Formula 2B]

[Chemical Formula 2C]

In Chemical Formulae 2A, 2B, and 2C, $X^5$ is O, S, Se, Te, or $NR^{aa}$, wherein $R^{aa}$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, $X^6$ is N, $R^5$, $R^6$, and $R^7$ are independently a halogen atom, a hydroxy group, a substituted or unsubstituted C1 to C30 alkyl group, a substituted or unsubstituted C1 to C30 alkoxy group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a combination thereof, a is an integer of 0 to 3, b is an integer of 0 to 4, c is an integer of 0 to 4, $R^a$ and $R^b$ are independently hydrogen or a C1 to C6 alkyl group, m is 0 to 20, and when m is 2 or more, —$(CR^aR^b)$— is optionally replaced by —O—, —C(=O)—, —OC(=O)O—, or —C(=O)O—, $R^c$ and $R^d$ are independently hydrogen or a C1 to C6 alkyl group, n is 0 to 20, and when n is 2 or more, —$(CR^bR^d)$— is optionally replaced by —O—, —C(=O), —OC(=O)O—, or —C(=O)O—, $R^e$ and $R^f$ are independently hydrogen or a C1 to C6 alkyl group, r is 0 to 20, when r is 2 or more, —$(CR^eR^f)$— is optionally replaced by —O—, —C(O)—, —OC(=O)O—, or —C(=O)O—, and

* is a linking point.

$R^1$ to $R^4$ may be specifically selected from Group 1 or Group 2.

[Group 1]

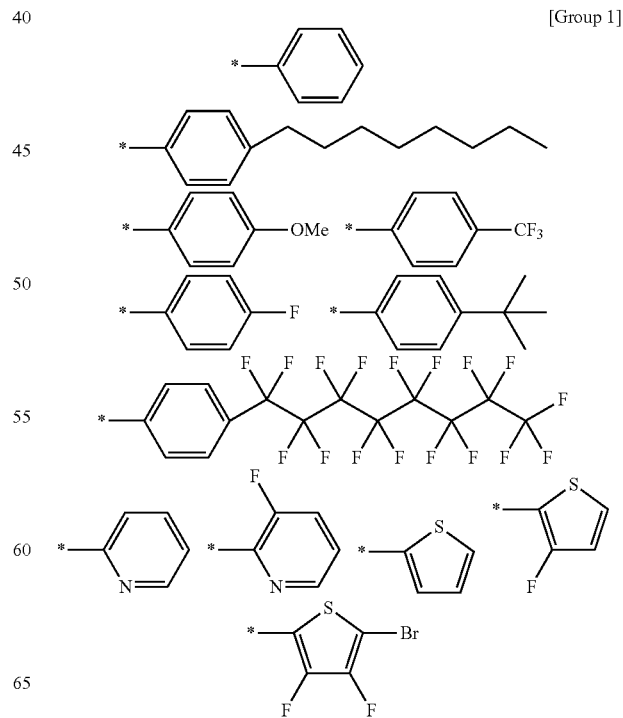

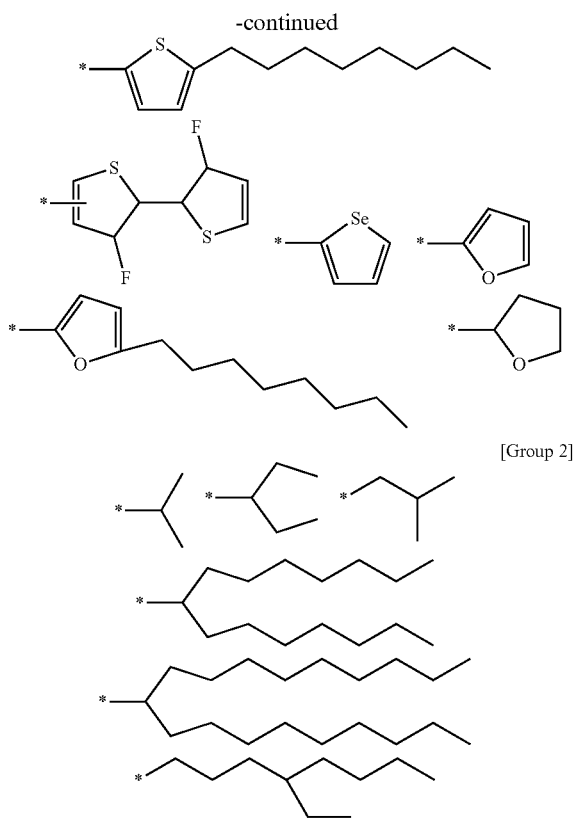

[Group 2]

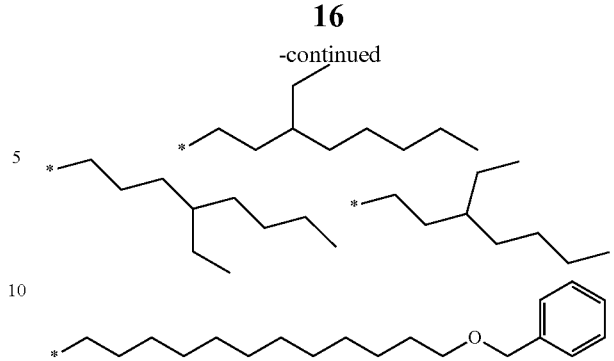

The condensed polycyclic heteroaromatic compound according to an embodiment may have an average molecular weight of about 300 to about 5,000, about 300 to about 4,000, or about 300 to about 3,000. When the average molecular weight is within the ranges, it is easy to handle.

The organic compound may have liquid crystal characteristics in a desired and/or alternatively predetermined temperature region by disposing the aliphatic chain group and the cyclic group 'asymmetrically' at both sides of the core. The organic compound may exhibit smectic liquid crystal characteristics according to heat-treatment at a desired and/or alternatively predetermined temperature and thus molecular alignment properties may be increased and charge mobility may further be increased when the organic compound is applied and annealed for example to a thin film transistor using a solution process. Herein the annealing may be performed at about 200° C. to about 250° C.

Specific examples of the organic compound may be compounds of Group 3, but are not limited thereto.

[Group 3]

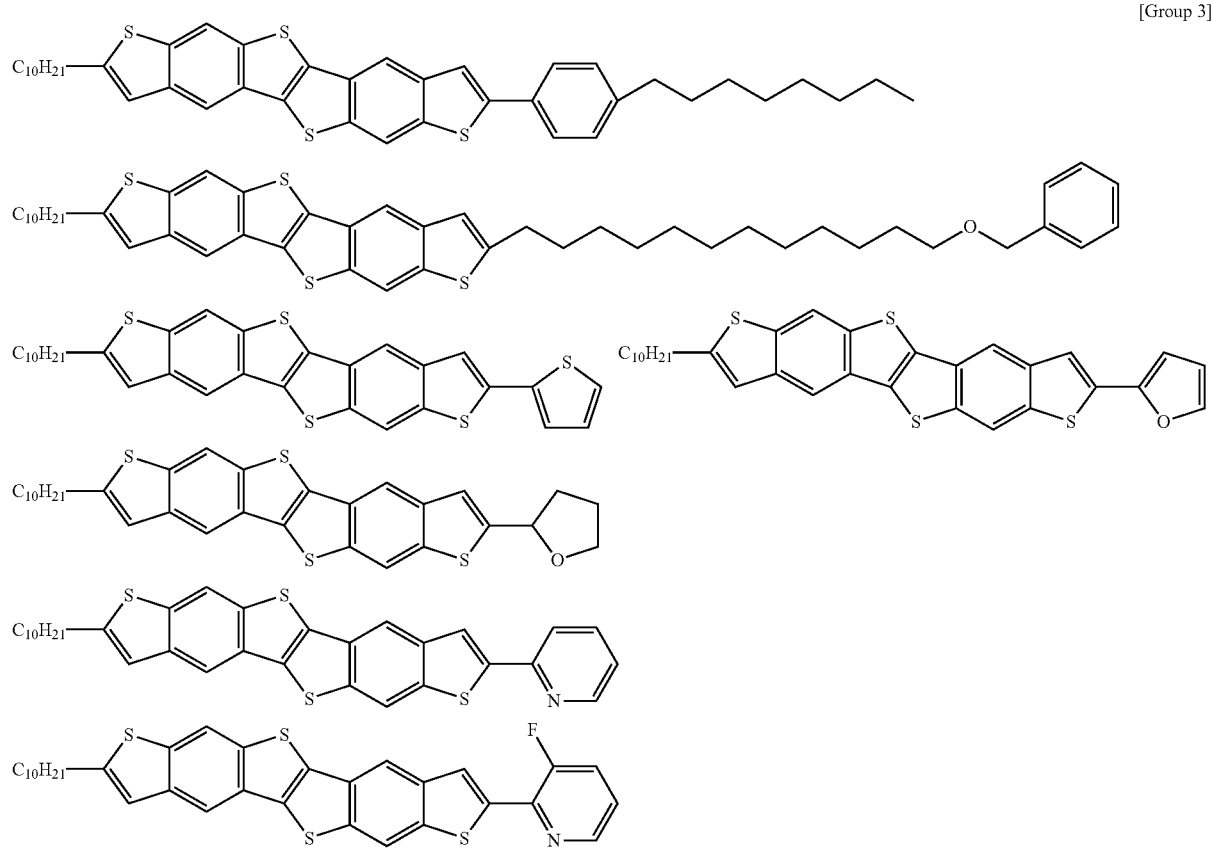

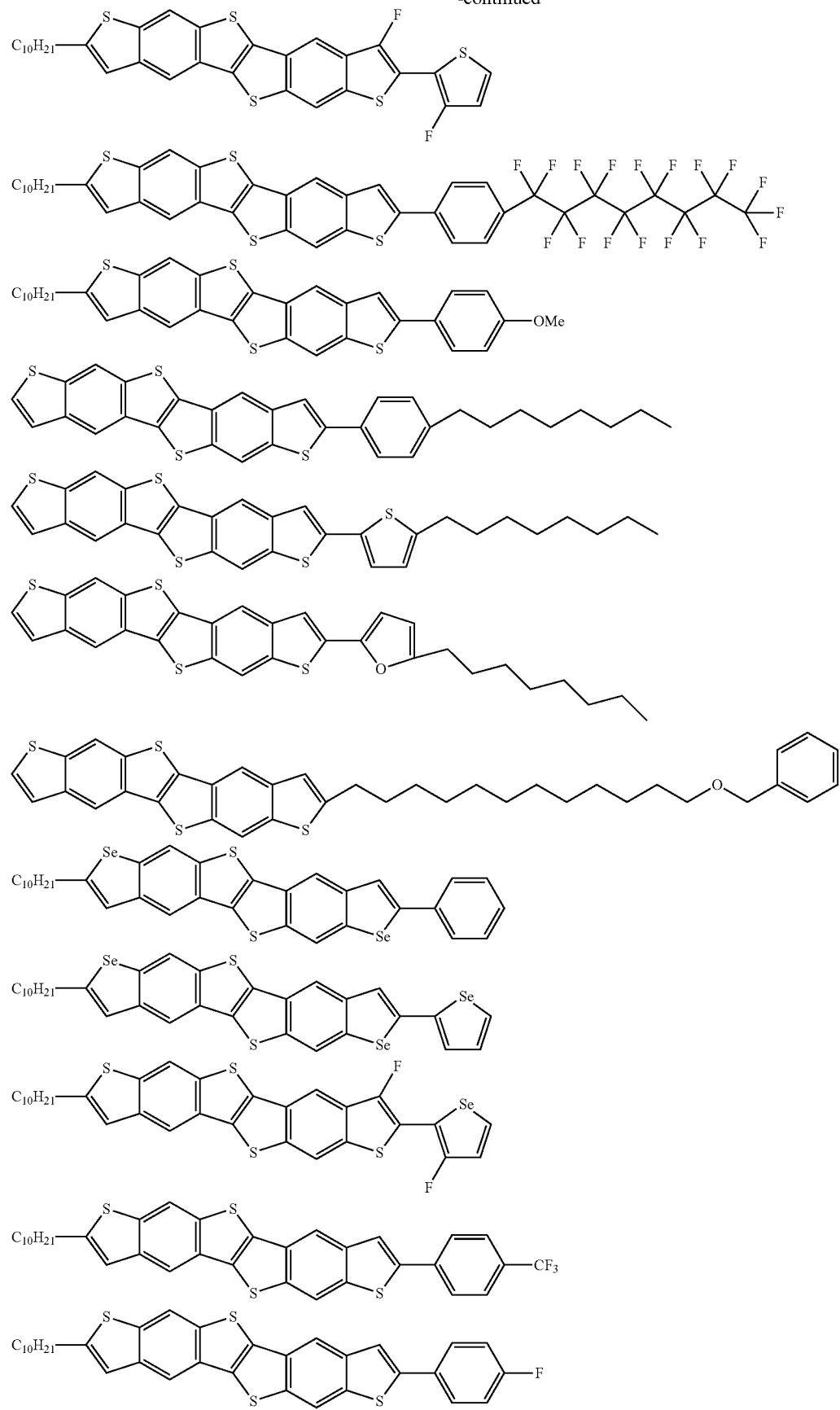

-continued
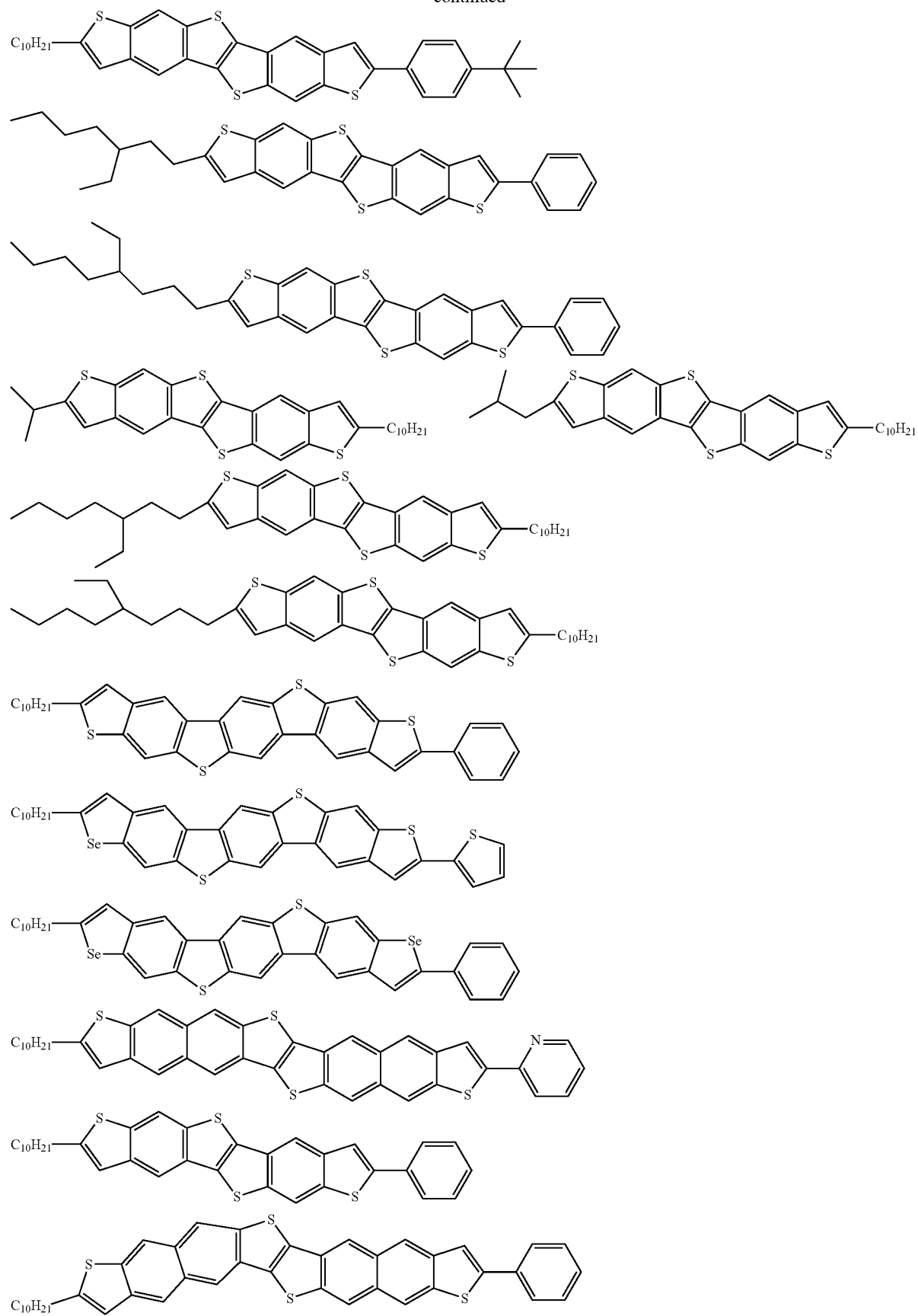

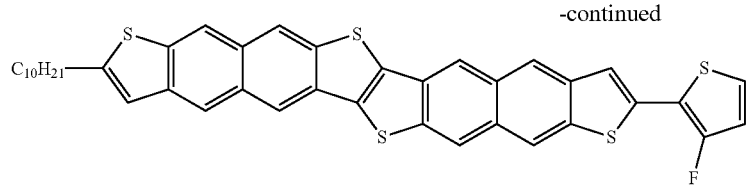

-continued

The organic compound may be implemented into an organic thin film by a deposition or solution process. The organic thin film may be applied to various devices including an organic semiconductor. For example, the organic compound may be applied to an organic thin film transistor, and may be applied to a charge transport layer and/or an active layer of an electronic device such as a solar cell, an organic light emitting diode (OLED) display, and an organic sensor.

Hereinafter, one example of an organic thin film transistor including the organic compound is described referring to the drawings.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view showing an organic thin film transistor according to an embodiment.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride (SiN) and a silicon oxide ($SiO_2$).

A source electrode 173 and a drain electrode 175 are formed on the gate insulating layer 140. The source electrode 173 and the drain electrode 175 face each other with the active layer 154 therebetween. The source electrode 173 is electrically connected to the data line (not shown) transferring the data signal. The source electrode 173 and the drain electrode 175 may be made of gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the organic compound. The organic semiconductor 154 may be formed by preparing the organic compound in a form of a solution and coating it using a solution process for example spin coating, slit coating, or inkjet printing. However, it may be formed by a dry process such as deposition of the organic compound.

Although an organic thin film transistor having a bottom gate structure is described as an example of an organic thin film transistor, it is not limited thereto, and it may be applied to all organic thin film transistors such as an organic thin film transistor having a top gate structure. For example, in an embodiment, an organic thin film transistor having a top gate structure may include the substrate 100; the source electrode 173 and the drain electrode 175 spaced apart from each other on the substrate 110; the organic semiconductor 154 covering the substrate 110, the source electrode 173 and the drain electrode 175; the gate insulating layer 140 covering the organic semiconductor 154; and the gate electrode 124 on the gate insulating layer 140 over a portion of the substrate that is between the source electrode 173 and the drain electrode 175.

The organic thin film transistor may be applied to a switch or driving device of various electronic devices, and the electronic device may be, for example, a liquid crystal display (LCD), an organic light emitting diode (OLED) display, an eletrophoretic display device, and an organic sensor.

Hereinafter, inventive concepts are described in more detail with reference to examples. However, these examples are non-limiting examples, and inventive concepts are not limited thereto.

Synthesis of Organic Compounds

Synthesis Example 1

[Reaction Scheme 1]

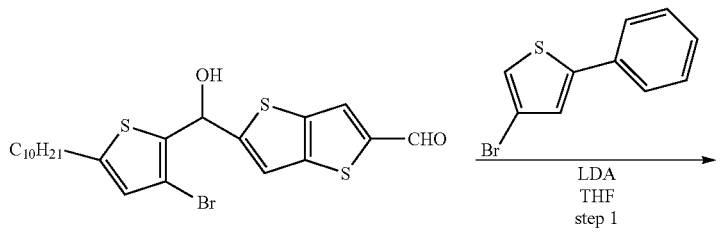

LDA
THF
step 1

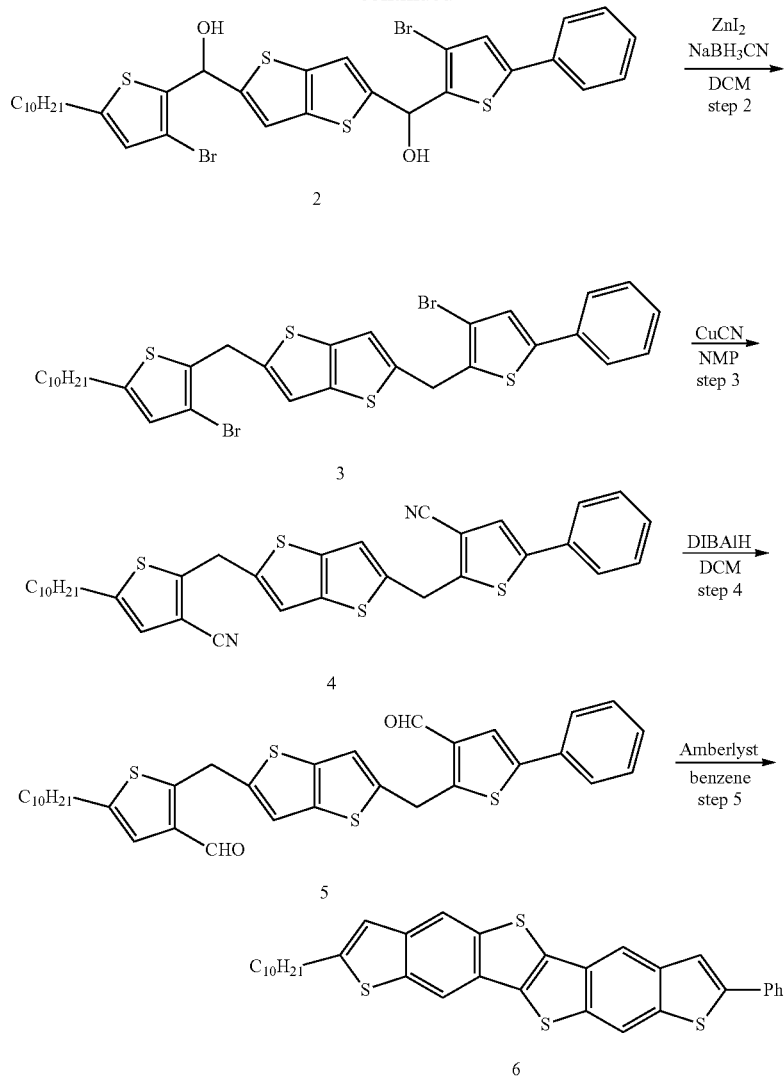

(1) (5-((3-bromo-5-decylthiophen-2-yl)methyl)thieno[3,2-b]thiophen-2-yl)(3-bromo-5-phenylthiophen-2-yl)methanol) (Synthesis of Compound 2)

4-bromo-2-phenylthiophene (6 g, 25.1 mmol) is dissolved in 300 mL dry tetrahydrofuran (THF) and then cooled down to −78° C. LDA (2M solution) (15.1 ml, 30 mmol) is slowly added in a dropwise fashion thereto, and Compound 1 (12.1 g, 25.1 mmol) is added thereto. The temperature is slowly increased, and the resultant is stirred at room temperature for 12 hours. 100 mL of an ammonium chloride saturated solution is added thereto and extracted with ethyl acetate and washed with water several times. The resultant is dried and filtered with magnesium sulfate, then the ethylacetate solvent is removed, and the resultant is purified with a silica column chromatography to obtain Compound 2. (A yield of 67%)

$^1$H NMR (500 MHz, CDCl$_3$): δ ppm 7.53 (d, 2H), 7.43 (m, 2H), 7.31 (d, 1H), 7.17 (s, 1H), 7.13 (s, 1H), 7.01 (s, 1H), 6.6 (s, 1H), 6.37 (d, 1H), 4.26 (s, 2H), 2.68 (t, 2H), 1.58 (m, 2H), 1.27 (m, 14H), 0.87 (t, 3H)

(2) 2-((3-bromo-5-decylthiophen-2-yl)methyl)-5-((3-bromo-5-phenylthiophen-2-yl)methyl)thieno[3,2-b]thiophene (Synthesis of Compound 3)

The compound (10 g, 13.84 mmol) is dissolved in 700 mL of dichloromethane and ZnI$_2$ (7.07 g, 23.5 mmol) and NaCNBH$_3$ (6.09 g, 96.86 mmol) are slowly added thereto. The mixture is stirred at room temperature for 24 hours and passed through a Celite pad. A filtrate is washed with an ammonium chloride saturated solution and water, respectively and is dried with MgSO$_4$ and concentrated under reduced pressure to obtain yellow oil. The obtained material is purified with a silica column chromatography to obtain Compound 3. (A yield of 92%)

$^1$H NMR (500 MHz, CDCl$_3$): δ ppm 7.50 (d, 2H), 7.35 (m, 2H), 7.28 (m, 1H), 7.13 (s, 1H), 7.03 (s, 1H), 7.0 (s, 1H), 6.6 (s, 1H), 6.37 (d, 1H), 4.33 (s, 2H), 4.26 (s, 2H), 2.69 (t, 2H), 1.55 (m, 2H), 1.27 (m, 14H), 0.87 (t, 3H)

(3) 2-((5-((3-cyano-5-decylthiophen-2-yl)methyl)thieno[3,2-b]thiophen-2-yl)methyl)-5-phenylthiophene-3-carbonitrile (Synthesis of Compound 4)

The compound (9 g, 12.73 mmol) is dissolved in 135 ml of N-methylpyrrolidone, copper cyanide (CuCN) (3.42 g, 38.2 mmol) is added thereto, and then the resultant is reacted in a microwave reactor under a condition of 50 W and 185° C. for 2 hours. After the reaction is completed, a 1N HCl solution is poured and then the resultant is stirred for 30 minutes. A solid is filtered, extracted with chloroform (CHCl$_3$), and washed with water. The resultant is dried and filtered with magnesium sulfate, then the chloroform solvent is removed, and the resultant is purified with a silica column chromatography to obtain Compound 4. (A yield of 60%)

$^1$H NMR (500 MHz, CDCl$_3$): δ ppm 7.49 (d, 2H), 7.38 (m, 2H), 7.34 (d, 1H), 7.29 (s, 1H), 7.11 (s, 1H), 7.06 (s, 1H), 6.79 (s, 1H), 4.55 (s, 2H), 4.48 (s, 2H), 2.70 (t, 2H), 1.59 (m, 2H), 1.27 (m, 14H), 0.86 (t, 3H)

(4) 5-decyl-2-((5-((3-formyl-5-phenylthiophen-2-yl)methyl)thieno[3,2-b]thiophen-2-yl)methyl)thiophene-3-carbaldehyde (Synthesis of Compound 5)

The compound (4.56 g, 7.61 mmol) is dissolved in 600 mL of dichloromethane and is cooled down to 0° C. Diisobutylaluminium hydride (DIBALH, 1.0 M solution in cyclohexane) (18.27 ml, 18.27 mmol) is added and stirred for 2 hours. 5% citric acid is poured to terminate the reaction and the resultant is extracted with chloroform (CHCl$_3$) and washed with water and brine. Then, an organic layer is dried with MgSO$_4$ and concentrated under a reduced pressure, and then the material is purified with a silica chromatography to obtain Compound 5. (A yield of 67%)

$^1$H NMR (500 MHz, CDCl$_3$): δ ppm 10.1 (s, 1H), 9.99 (s, 1H), 7.59 (s, 1H), 7.55 (d, 2H), 7.37 (m, 2H), 7.31 (m, 1H), 7.06 (d, 2H), 7.01 (s, 1H), 4.76 (s, 2H), 4.69 (s, 2H), 2.71 (t, 2H), 1.62 (m, 2H), 1.28 (m, 14H), 0.87 (t, 3H)

(5) Synthesis of Compound 6

Compound 5 (3.1 g, 5.12 mmol) is dissolved in 300 mL of benzene, Amberlyst 15 (3.1 g) is added thereto, and water is removed using a Dean-Stark trap while the mixture is stirred and refluxed. After 24 hours, a pale yellow solid is precipitated. The temperature is lowered into room temperature, Amberlyst 15 is precipitated and floating materials are removed and filtered to obtain Compound 6 as a yellow solid. (A yield of 50%)

MS (MALDI-TOF-MS, m/z) 568.194 (M+)

Synthesis Example 2

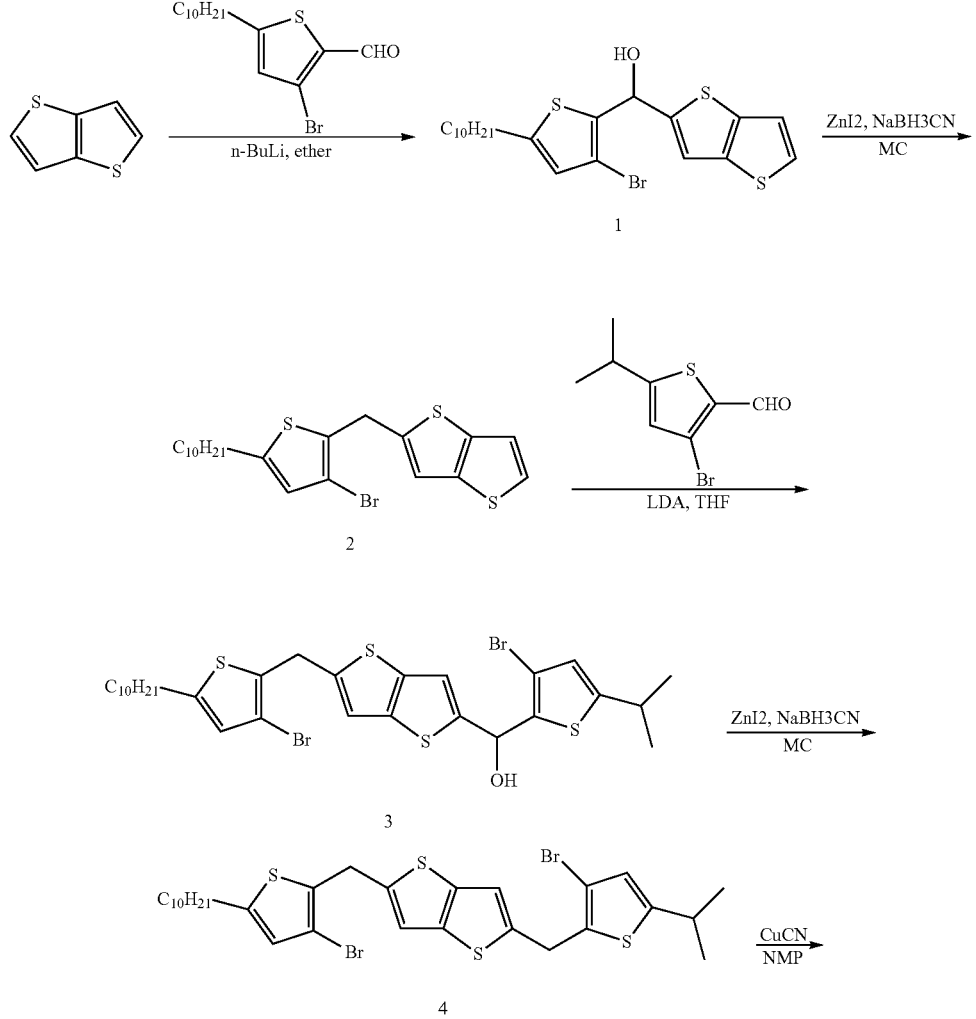

[Reaction Scheme 2]

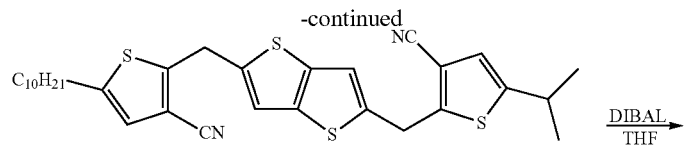

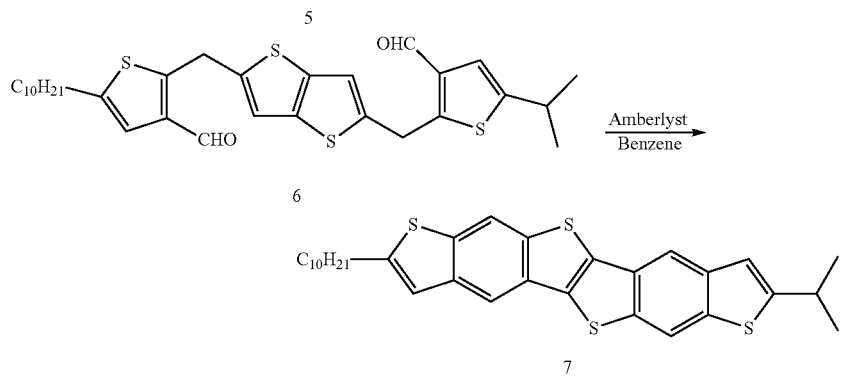

(1) 3-bromo-5-decylthiophen-2-yl)(thieno[3,2-b]thiophen-2-yl)methanol (Synthesis of Compound 1)

Thieno[3,2-b]thiophen (7.5 g, 53.5 mmol) is dissolved in dry ether and cooled down to 0° C. n-BuLi (25.7 mL, 64.2 mmol) is slowly added in a dropwise fashion and then 3-bromo-5-decyl-2-thiophencarboxyaldehyde (23.04 g, 69.5 mmol) is added thereto. The temperature is slowly increased and the resultant is stirred at room temperature for 12 hours. 200 mL of an ammonium chloride saturated solution is added thereto and the resultant is extracted with ethyl acetate and is washed with water several times. The resultant is dried and filtered with magnesium sulfate, then the ethylacetate solvent is removed, and the resultant is purified with a silica column chromatography to obtain Compound 1. (A yield of 90%)

$^1$H NMR (300 MHz, CDCl$_3$): δ ppm 7.34 (d, 1H), 7.22 (d, 1H), 7.21 (s, 1H), 6.64 (s, 1H), 6.38 (d, 1H), 2.74 (t, 2H), 2.67 (d, 1H), 1.64 (m, 2H), 1.27 (m, 14H), 0.88 (t, 3H)

(2) 2-(3-bromo-5-decylthiophen-2-yl)methylthieno[3,2-b]thiophene (Synthesis of Compound 2)

Compound 1 (22.6 g, 47.9 mmol) is dissolved in 1 L of dichloromethane, and then ZnI$_2$ (24.5 g, 76.7 mmol) and NaCNBH$_3$ (21.1 g, 335.5 mmol) are slowly added thereto. The mixture is stirred at room temperature for 24 hours, and then 200 mL of an ammonium chloride saturated solution is added thereto to terminate a reaction. The resultant is extracted with dichloromethane and washed with water several times. The resultant is dried with MgSO$_4$ and concentrated under a reduced pressure to obtain yellow oil. The material is purified with a silica column chromatography to obtain Compound 3. (A yield of 89%)

$^1$H NMR (300 MHz, CDCl$_3$): δ ppm 7.29 (d, 1H), 7.17 (d, 1H), 7.06 (s, 1H), 6.62 (s, 1H), 4.29 (s, 2H), 2.70 (t, 2H), 1.64 (m, 2H), 1.25 (m, 14H), 0.88 (t, 3H)

(3) 5-((3-bromo-5-decylthiophen-2-yl)methyl)thieno[3,2-b]thiophen-2-yl) (3-bromo-5-isopropylthiophen-2-yl)methanol (Synthesis of Compound 3)

Compound 2 (11.7 g, 25.6 mmol) is dissolved in 300 mL dry tetrahydrofuran (THF) and then cooled down to −78° C. LDA (2M solution) (16.7 ml, 33.4 mmol) is slowly added in a dropwise fashion, and 3-bromo-5-isopropyl-2-thiophencarboxyaldehyde (6.6 g, 28.3 mmol) is added thereto. The temperature is slowly increased and the resultant is stirred at room temperature for 12 hours. 100 mL of an ammonium chloride saturated solution is added thereto and is extracted with dichloromethane and washed with water several times. The resultant is dried and filtered with magnesium sulfate and is purified with a silica column chromatography to obtain Compound 2. (A yield of 49%)

$^1$H NMR (300 MHz, CDCl$_3$): δ ppm 7.12 (s, 1H), 7.01 (s, 1H), 6.65 (s, 1H), 6.61 (s, 1H), 6.35 (d, 1H), 4.27 (s, 2H), 3.09 (m, 1H), 2.70 (t, 2H), 2.65 (d, 1H), 1.60 (m, 2H), 1.27 (m, 20H), 0.88 (t, 3H)

(4) 2-((3-bromo-5-decylthiophen-2-yl)methyl)-5-((3-bromo-5-isopropylthiophen-2-yl)methyl)thieno[3,2-b]thiophene (Synthesis of Compound 4)

Compound 3 (8.2 g, 11.95 mmol) is dissolved in 1 L of dichloromethane and ZnI$_2$ (6.1 g, 19.1 mmol) and NaCNBH$_3$ (5.3 g, 83.7 mmol) are slowly added thereto. The mixture is stirred at room temperature for 24 hours and is washed with an ammonium chloride saturated solution and water, respectively, and is dried with MgSO$_4$ and concentrated under reduced pressure to obtain yellow oil. The obtained material is purified with a silica column chromatography to obtain Compound 4. (A yield of 98%)

$^1$H NMR (300 MHz, CDCl$_3$): δ ppm 6.97 (s, 2H), 6.61 (d, 2H), 4.27 (s, 4H), 3.09 (m, 1H), 2.68 (t, 2H), 1.60 (m, 2H), 1.27 (m, 20H), 0.88 (t, 3H)

(5) 2-((5-((3-cyano-5-decylthiophen-2-yl)methyl)thieno[3,2-b]thiophen-2-yl)methyl)-5-isopropylphenylthiophene-3-carbonitrile (Synthesis of Compound 5)

Compound 4 (8.2 g, 12.2 mmol) is dissolved in 120 ml of N-methylpyrrolidone, copper cyanide (CuCN) (4.2 g, 48.9 mmol) is added thereto, and then the resultant is reacted in a microwave reactor under a condition of 50 W and 180° C. for 2 hours. After the reaction is completed, a 1N HCl solution is poured and then the resultant is stirred for 30 minutes. A solid is filtered, extracted with dichloromethane, and washed with water. The resultant is dried with magnesium sulfate and is passed through a short path column using celite and silica to obtain Compound 5. (A yield of 81%)

$^1$H NMR (300 MHz, CDCl$_3$): δ ppm 7.05 (s, 2H), 6.80 (d, 2H), 4.46 (s, 4H), 3.09 (m, 1H), 2.69 (t, 2H), 1.60 (m, 2H), 1.27 (m, 20H), 0.88 (t, 3H)

(6) 5-decyl-2-((5-((3-formyl-5-isopropylthiophen-2-yl)methyl)thieno[3,2-b]thiophen-2-yl)methyl)thiophene-3-carbaldehyde (Synthesis of Compound 6)

Compound 5 (5.4 g, 9.6 mmol) is dissolved in 800 mL of dichloromethane and is cooled down to 0° C. Diisobutylaluminium hydride (DIBALH, 1.0 M solution in cyclohexane) (27.9 ml, 27.9 mmol) is added and stirred for 5 minutes. A reaction solution is poured in to a mixed solution of methanol and water (methanol:water=2:1) to terminate a reaction, the resultant is extracted with dichloromethane and washed with water and brine, an organic layer is dried with MgSO$_4$ and concentrated under a reduced pressure, and the material is purified with a silica chromatography to obtain Compound 6. (A yield of 91%)

$^1$H NMR (300 MHz, CDCl$_3$): δ ppm 10.0 (s, 2H), 7.09 (s, 1H), 7.06 (s, 1H) 7.00 (s, 2H), 4.68 (s, 4H), 3.07 (m, 1H), 2.71 (t, 2H), 1.63 (m, 2H), 1.28 (m, 20H), 0.88 (t, 3H)

(7) Synthesis of Compound 7

Compound 6 (5.0 g, 8.8 mmol) is dissolved in 300 mL of benzene, Amberlyst 15 (4.0 g) is added thereto, and water is removed using a Dean-Stark trap while the mixture is stirred and refluxed. After 24 hours, a temperature of a pale yellow liquid is lowered into room temperature to produce a white precipitate. Precipitated floating materials are filtered, recovered, and then recrystallization-purified in a mixed solution of hexane and chloroform to obtain Compound 7 as a white solid. (A yield of 72%)

$^1$H NMR (300 MHz, CDCl$_3$): δ ppm 8.27 (s, 2H), 8.12 (s, 2H) 7.12 (s, 1H), 7.10 (s, 1H), 3.28 (m, 1H), 2.93 (t, 2H), 1.78 (m, 2H), 1.44 (d, 6H), 1.27 (m, 14H) 0.87 (t, 3H)

MS (MALDI-TOF-MS, m/z) 534.249 (M+)

Synthesis Example 3

[Reaction Scheme 3]

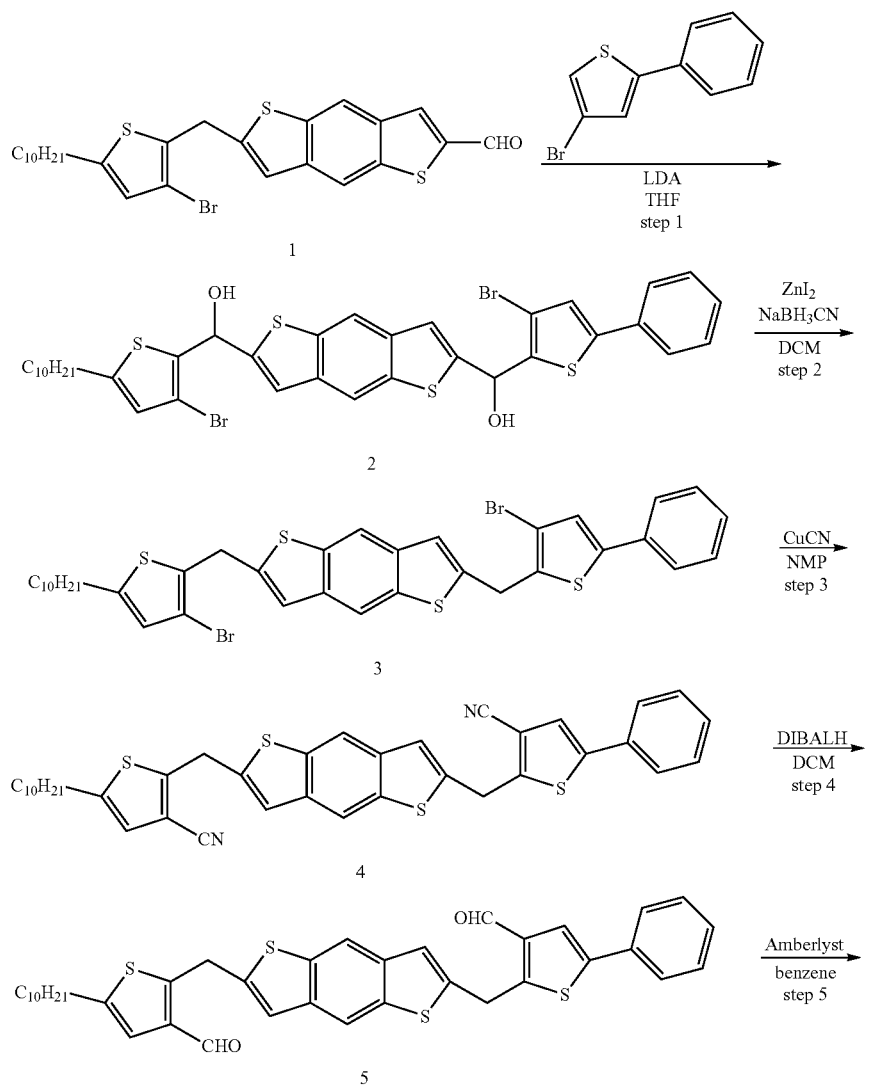

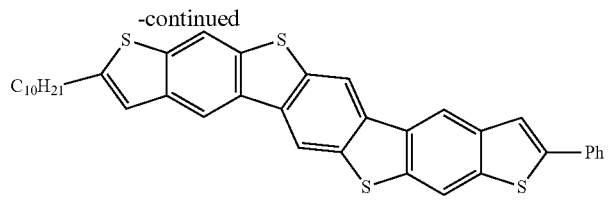

6

(1) (3-bromo-5-decylthiophen-2-yl) (6-((3-bromo-5-phenylthiophen-2-yl) (hydroxy)methyl)benzo[1,2-b:4,5-b']dithiophen-2-yl)methanol (Synthesis of Compound 2)

4-bromo-2-phenylthiophene (4-bromo-2-phenylthiophene) (6 g, 25.1 mmol) is dissolved in 300 mL of dry tetrahydrofuran (THF) and then cooled down to −78° C. LDA (2M solution) (15.1 ml, 30 mmol) is slowly added in a dropwise fashion and Compound 1 (19.8 g, 25.1 mmol) is added thereto. The temperature is slowly increased and the resultant is stirred at room temperature for 12 hours. 100 mL of an ammonium chloride saturated solution is added thereto and is extracted with ethyl acetate and washed with water several times. The resultant is dried and filtered with magnesium sulfate, then the ethylacetate solvent is removed, and the resultant is purified with a silica column chromatography to obtain Compound 2. (A yield of 65%)

(2) 2-((3-bromo-5-decylthiophen-2-yl)methyl)-6-((3-bromo-5-phenylthiophen-2-yl)methyl)benzo[1,2-b:4,5-b']dithiophene (Synthesis of Compound 3)

The compound (10 g, 12.68 mmol) is dissolved in 700 mL of dichloromethane, and $ZnI_2$ (6.88 g, 21.56 mmol) and $NaCNBH_3$ (5.58 g, 88.76 mmol) are slowly added thereto. The mixture is stirred at room temperature for 24 hours and passed through a Celite pad. A filtrate is washed with an ammonium chloride saturated solution and water, respectively and is dried with $MgSO_4$ and concentrated under reduced pressure to obtain yellow oil. The obtained material is purified with a silica column chromatography to obtain Compound 3. (A yield of 90%)

(3) 2-((6-((3-cyano-5-decylthiophen-2-yl)methyl)benzo[1,2-b:4,5-b']dithiophen-2-yl)methyl)-5-phenylthiophene-3-carbonitrile (Synthesis of Compound 4)

The compound (9 g, 11.89 mmol) is dissolved in 135 ml of N-methylpyrrolidone, copper cyanide (CuCN) (3.19 g, 35.68 mmol) is added thereto, and then the resultant is reacted in a microwave reactor under a condition of 50 W and 185° C. for 2 hours. After the reaction is completed, a 1N HCl solution is poured and then the resultant is stirred for 30 minutes. A solid is filtered, extracted with chloroform ($CHCl_3$), and washed with water. The resultant is dried and filtered with magnesium sulfate, then the chloroform solvent is removed, and the resultant is purified with a silica column chromatography to obtain Compound 4. (A yield of 65%)

(4) 5-decyl-2-((6-((3-formyl-5-phenylthiophen-2-yl)methyl)benzo[1,2-b:4,5-b']dithiophen-2-yl)methyl)thiophene-3-carbaldehyde (Synthesis of Compound 5)

The compound (5 g, 7.70 mmol) is dissolved in 600 mL of dichloromethane and is cooled down to 0° C. Diisobutylaluminium hydride (DIBALH, 1.0 M solution in cyclohexane) (18.48 ml, 18.48 mmol) is added and stirred for 2 hours. 5% citric acid is poured to terminate the reaction, the resultant is extracted with chloroform ($CHCl_3$) and washed with water and brine, an organic layer is dried with MgSO4 and concentrated under a reduced pressure, and then the material is purified with a silica chromatography to obtain Compound 5. (A yield of 65%)

(5) Synthesis of Compound 6

Compound 5 (3.5 g, 5.34 mmol) is dissolved in 300 mL of benzene, Amberlyst 15 (3.1 g) is added thereto, and water is removed using a Dean-Stark trap while the mixture is stirred and refluxed. After 24 hours, a pale yellow solid is precipitated. The temperature is lowered into room temperature, Amberlyst 15 is precipitated and floating materials are removed and filtered to obtain Compound 6 as a yellow solid. (A yield of 50%)

Synthesis Example 4

[Reaction Scheme 4]

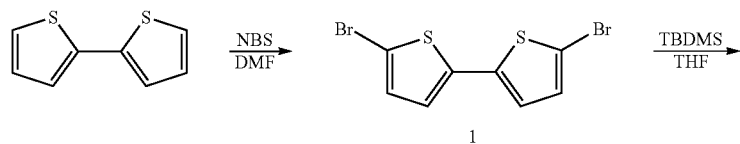

1

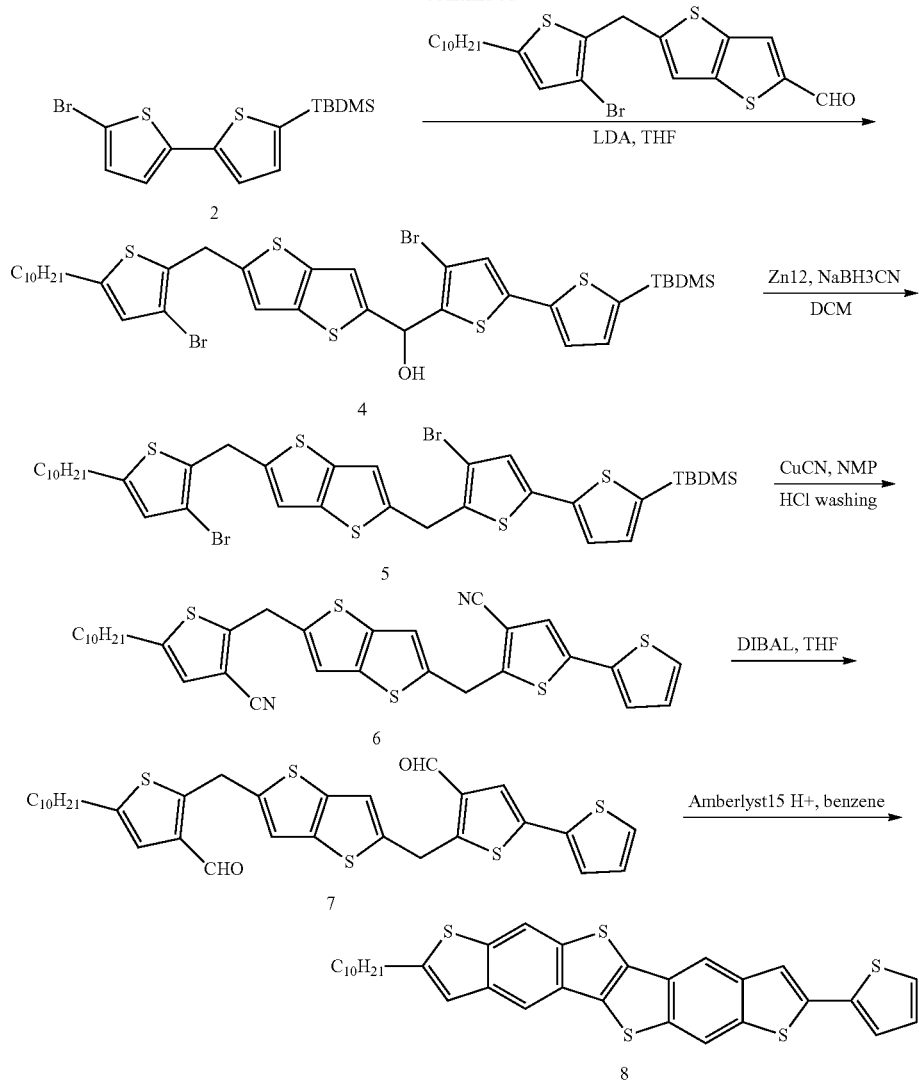

1. 5,5'-dibromo-2,2'-bithiophene (Synthesis of Compound 1)

2,2'-bithiophene (11.7 g, 70.1 mmol) is dissolved in 500 mL of N,N-dimethylmethanamide, and N-bromo succinimide (31 g, 175.2 mmol) is added in a dropwise fashion to bromide it. Then, the resultant is refluxed for 2 hours, water (1 L) is added thereto, and the produced precipitate is filtered and recovered. The recovered powder is dissolved in chloroform (700 mL), washed with water, and then dried with magnesium sulfate followed by evaporating the resultant. The resultant is washed with n-hexane and dried to obtain Compound 1 (A yield of 93%).

1H-NMR (300 MHz, CDCl$_3$): δ 6.96 (d, J=3.6 Hz, 1H), 6.85 (d, J=3.6 Hz, 1H)

2. (5'-bromo-[2,2'-bithiophen]-5-yl)(tert-butyl)dimethylsilane (Synthesis of Compound 2)

2,5-dibromo-bithiophene (20.3 g, 62.6 mmol) is put in 1.7 L of tetrahydrofuran to prepare a cold solution (−78° C.), n-butyllithium (2.5 M in hexane, 30 mL, 1.2 eq.) is added to the solution, and the reaction mixture is fervently stirred for 30 minutes. Subsequently, t-butyldimethylsilyl chloride (10.3 g, 68.9 mmol, 1.1 eq.) is added thereto. The obtained reaction mixture is stirred at −78° C. overnight, diluted with dichloromethane, and then washed with water and brine several times. Then, an organic layer therein is dried and evaporated with magnesium sulfate, and a yellow liquid therefrom is purified with a silica column chromatography to obtain 16.9 g of a while solid. (A yield of 75.3%)

1H-NMR (300 MHz, CDCl$_3$): δ 7.17 (d, J=3.3 Hz, 1H), 7.12 (d, J=3.3 Hz, 1H), 6.96 (d, J=3.9 Hz, 1H), 6.85 (d, J=3.9 Hz, 1H) 0.94 (s, 9H), 0.29 (s, 6H)

3. (4-bromo-5'-(tert-butyldimethylsilyl)-[2,2'-bithiophen]-5-yl)(5-((3-bromo-5-decylthiophen-2-yl)methyl)thieno[3,2-b]thiophen-2-yl)methanol) (Synthesis of Compound 4)

Compound 2 (8.9 g, 24.9 mmol) is added to 1.3 L of dry tetrahydrofuran to prepare a solution (−78° C.), lithium diisopropylamide (2.0 M in THF/heptane/ethylbenezene, 18.7 mL, 37.2 mmol) is added thereto, and the obtained reaction mixture is fervently stirred at −78° C. for 2 hours. Subsequently, Compound 3 (12.0 g, 24.9 mmol) is added thereto, the obtained mixture is slowly heated up to room temperature and then, stirred for 20 minutes, and a saturated ammonium chloride solution is added thereto. Next, the solution is diluted with dichloromethane and several times washed with water, and an organic layer is dried and evaporated with magnesium sulfate to obtain a brown liquid. The brown liquid is purified with a silica column chromatography to obtain Compound 4. (A yield of 59%)

$^1$H-NMR (300 MHz, CDCl$_3$): δ 7.21 (d, J=3.6 Hz, 1H), 7.17 (s, 1H), 7.12 (d, J=3.6 Hz, 1H), 7.02 (s, 1H), 7.02 (s, 1H), 6.61 (s, 1H), 6.36 (d, J=3.6 Hz, 1H), 4.27 (s, 2H), 2.70 (t, J=7.2 Hz, 2H), 2.66 (d, J=3.6 Hz, 1H), 1.62 (m, 2H), 1.25 (m, 14H), 0.92 (s, 9H), 0.87 (t, J=6.6 Hz, 3H), 0.29 (s, 6H)

4. (4'-bromo-5'-((5-((3-bromo-5-decylthiophen-2-yl)methyl)thieno[3,2-b]thiophen-2-yl)methyl)-[2,2'-bithiophen]-5-yl)(tert-butyl)dimethylsilane (Synthesis of Compound 5)

Compound 4 (13.6 g, 16.1 mmol) is dissolved in 1 L of dichloromethane and then ZnI$_2$ (8.2 g, 25.8 mmol) and NaCNBH$_3$ (7.1 g, 112.9 mmol) are slowly added thereto. The mixture is stirred at room temperature for 6 hours, and then 200 mL of an ammonium chloride saturated solution is added thereto to terminate a reaction. The resultant is extracted with dichloromethane and washed with water several times. The resultant is dried with MgSO$_4$ and concentrated under a reduced pressure to obtain yellow oil. The material is purified with a silica column chromatography to obtain Compound 3. (A yield of 94%)

$^1$H NMR (300 MHz, CDCl$_3$): δ ppm 7.15 (d, 1H), 7.10 (d, 1H), 7.02 (s, 1H), 7.01 (s, 1H), 6.61 (s, 1H), 4.30 (s, 2H), 4.26 (s, 2H), 2.70 (t, 2H), 1.67 (m, 2H), 1.25 (m, 14H), 0.92 (s, 9H), 0.88 (t, 3H), 0.30 (s, 6H)

5. 5-((5-((3-cyano-5-decylthiophen-2-yl)methyl)thieno[3,2-b]thiophen-2-yl)methyl)-[2,2'-bithiophene]-4-carbonitrile (Synthesis of Compound 6)

Compound 5 (11.6 g, 14.0 mmol) is dissolved in 120 ml of N-methylpyrrolidone, copper cyanide (CuCN) (4.9 g, 56.1 mmol) is added thereto to prepare a mixed solvent, and then, the mixed solvent is divided into 15 mL, and each is reacted in a microwave reactor under a condition of 50 W and 180° C. for 2 hours. After the reaction is completed, a 1N HCl solution is poured and then the resultant is stirred for 30 minutes. The solid is filtered, extracted with dichloromethane, and washed with water. Then, an organic layer therein is dried and evaporated with magnesium sulfate to obtain brown liquid. The brown liquid is purified with a silica column chromatography to obtain Compound 6. (A yield of 54%)

$^1$H NMR (300 MHz, CDCl$_3$): δ ppm 7.27 (d, 1H), 7.15 (s, 1H), 7.14 (d, 1H), 7.10 (s, 1H), 7.06 (s, 1H), 7.01 (m, 1H), 6.79 (s, 1H), 4.52 (s, 2H), 4.47 (s, 2H), 2.70 (t, 2H), 1.63 (m, 2H), 1.25 (m, 14H), 0.87 (t, 3H)

6. 5-((5-((5-decyl-3-formylthiophen-2-yl)methyl)thieno[3,2-b]thiophen-2-yl)methyl)-[2,2'-bithiophene]-4-carbaldehyde (Synthesis of Compound 7)

Compound 6 (4.6 g, 7.6 mmol) is dissolved in 800 mL of dichloromethane and is cooled down to 0° C. Diisobutylaluminium hydride (DIBALH, 1.0 M solution in cyclohexane) (22.8 ml, 22.8 mmol) is added and stirred for 5 minutes. A reaction solution is poured in to a mixed solution of methanol and water (methanol:water=2:1) to terminate a reaction, the resultant is extracted with dichloromethane and washed with water and brine, an organic layer is dried with MgSO$_4$ and concentrated under a reduced pressure, and the material is purified with a silica chromatography to obtain Compound 6. (A yield of 56%)

$^1$H NMR (300 MHz, CDCl$_3$): δ 10.04 (s, 1H), 9.99 (s, 1H), 7.43 (s, 1H), 7.24 (d, 1H) 7.13 (s, 1H), 7.06 (s, 1H), 7.05 (s, 1H), 7.02 (s, 1H), 7.00 (m, 1H), 4.73, (s, 2H), 4.69 (s, 2H), 2.71 (t, 2H), 1.62 (m, 2H), 1.25 (m, 14H), 0.87 (t, 3H)

7. Synthesis of Compound 8

Compound 7 (2.5 g, 4.1 mmol) is dissolved in 350 mL of benzene, Amberlyst 15 (5.2 g) is added thereto, and water is removed using a Dean-Stark trap while the mixture is stirred and refluxed. After 24 hours, a temperature of a pale yellow liquid is lowered into room temperature to produce a precipitate. Precipitated floating materials are filtered, recovered, and then washed with benzene, MC, EA, THF, and MC to obtain Compound 7. (A yield of 61%)

MS (MALDI-TOF-MS, m/z) 574.224 (M+)

Synthesis Example 5

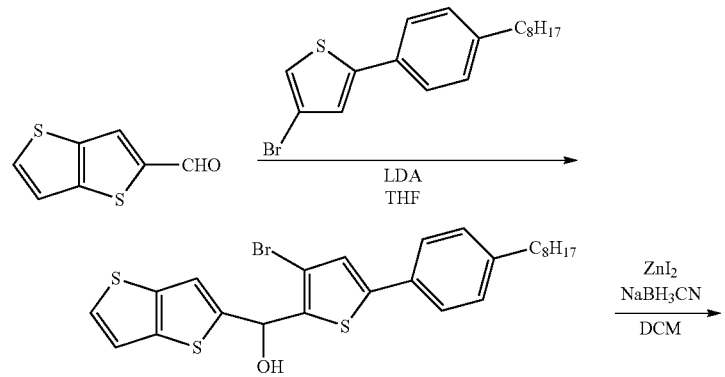

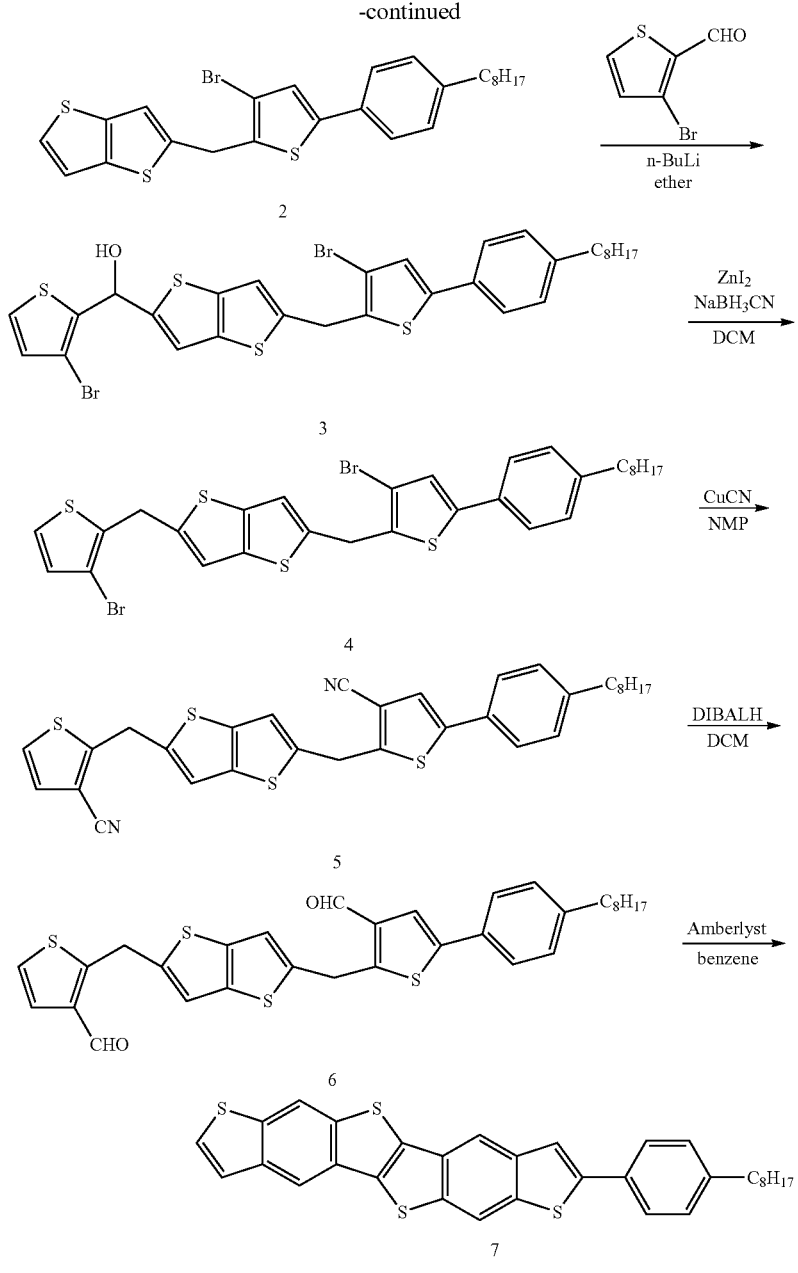

1. (3-bromo-5-(4-octylphenyl)thiophen-2-yl) (thieno[3,2-b]thiophen-2-yl)methanol (Synthesis of Compound 1)

4-bromo-2-(4-octylphenyl)thiophene (7.04 g, 20.0 mmol) dissolved in dry tetrahydrofuran (THF) and then cooled down to −78° C. LDA (2M solution) (12.02 ml, 24 mmol) is slowly added in a dropwise fashion and thieno[3,2-b]thiophene-2-carbaldehyde (3.07 g, 20.0 mmol) is added thereto. The temperature is slowly increased and the resultant is stirred at room temperature for 12 hours. 100 mL of an ammonium chloride saturated solution is added thereto and is extracted with ethyl acetate and washed with water several times. The resultant is dried and filtered with magnesium sulfate, then the ethylacetate solvent is removed, and the resultant is purified with a silica column chromatography to obtain Compound 1. (A yield of 89%)

2. 2-(3-bromo-5-(4-octylphenyl)thiophene-2-yl) methyl)thieno[3,2-b]thiophene (Synthesis of Compound 2)

Compound 1 (9.26 g, 17.8 mmol) is dissolved in 1 L of dichloromethane and $ZnI_2$ (9.10 g, 28.5 mmol) and $NaCNBH_3$ (7.84 g, 124.8 mmol) are slowly added thereto. The mixture is stirred at room temperature for 24 hours, and then 200 mL of an ammonium chloride saturated solution is added thereto to terminate a reaction. The resultant is extracted with dichloromethane and washed with water several times. The resultant is dried with $MgSO_4$ and concentrated under a reduced pressure to obtain yellow oil. The material is purified with a silica column chromatography to obtain Compound 3. (A yield of 89%)

3. (3-bromo-5-(4-octylphenyl)thiophen-2-yl) (5-((3-bromothiophen-2-yl)methyl)thieno[3,2-b]thiophen-2-yl)methanol (Synthesis of Compound 3)

Compound 2 (8.63 g, 17.1 mmol) is dissolved in 300 mL of dry tetrahydrofuran (THF) and then cooled down to −78° C. LDA (2M solution) (10.3 ml, 20.6 mmol) is slowly added in a dropwise fashion, and 3-bromothiophene-2-carbaldehyde (3.6 g, 18.9 mmol) is added thereto. The temperature is slowly increased and the resultant is stirred at room temperature for 12 hours. 100 mL of an ammonium chloride saturated solution is added thereto and is extracted with dichloromethane and washed with water several times. The resultant is dried and filtered with magnesium sulfate and is purified with a silica column chromatography to obtain Compound 2. (A yield of 49%)

4. 2-((3-bromo-5-(4-octylphenyl)thiophen-2-yl)methyl)-5-((3-bromothiophen-2-yl)methyl)thieno[3,2-b]thiophene (Synthesis of Compound 4)

Compound 3 (5.2 g, 7.4 mmol) is dissolved in 1 L of dichloromethane and $ZnI_2$ (3.8 g, 11.9 mmol) and $NaCNBH_3$ (3.3 g, 52.1 mmol) are slowly added thereto. The mixture is stirred at room temperature for 24 hours and is washed with an ammonium chloride saturated solution and water, respectively, and is dried with $MgSO_4$ and concentrated under reduced pressure to obtain yellow oil. The obtained material is purified with a silica column chromatography to obtain Compound 4. (A yield of 98%)

5. 2-((5-((3-cyanothiophen-2-yl)methyl)thieno[3,2-b]thiophen-2-yl)methyl)-5-(4-octylphenyl)thiophene-3-carbonitrile (Synthesis of Compound 5)

Compound 4 (0.3 g, 0.44 mmol) is dissolved in 6 ml of N-methylpyrrolidone, copper cyanide (CuCN) (0.16 g, 1.8 mmol) is added thereto, and then the resultant is reacted in a microwave reactor under a condition of 50 W and 180° C. for 2 hours. After the reaction is completed, a 1N HCl solution is poured and then the resultant is stirred for 30 minutes. A solid is filtered, extracted with dichloromethane, and washed with water. The resultant is dried with magnesium sulfate and is passed through a short path column using celite and silica to obtain Compound 5. (A yield of 81%)

6. 2-((5-((3-formylthiophen-2-yl)methyl)thieno[3,2-b]thiophen-2-yl)methyl)-5-(4-octylphenyhthiophene-3-carbaldehyde (Synthesis of Compound 6)

Compound 5 (1.6 g, 4.2 mmol) is dissolved in 200 mL of dichloromethane and is cooled down to 0° C. Diisobutyl-aluminium hydride (DIBALH, 1.0M solution in cyclohexane) (10.1 ml, 10.1 mmol) is added and stirred for 4 hours. A reaction solution is poured in to a mixed solution of methanol and water (methanol:water=2:1) to terminate a reaction, the resultant is extracted with dichloromethane and washed with water and brine, an organic layer is dried with $MgSO_4$ and concentrated under a reduced pressure, and the material is purified with a silica chromatography to obtain Compound 6. (A yield of 91%)

7. Synthesis of Compound 7

Compound 6 (1.1 g, 1.9 mmol) is dissolved in 100 mL of benzene Amberlyst 15 (1.1.0 g) is added thereto, and water is removed using a Dean-Stark trap while the mixture is stirred and refluxed. After 24 hours, the temperature of the produced pale yellow liquid is lowered into room temperature to obtain a white precipitate. Precipitated floating materials are collected by using a filter, and a filtrate therefrom is recrystallization-purified in a mixed solution of hexane and chloroform to obtain Compound 7 as a white solid. (A yield of 72%)
MS (MALDI-TOF-MS, m/z) 540.11 (M+)

Comparative Synthesis Example 1

[Reaction Scheme 1A]

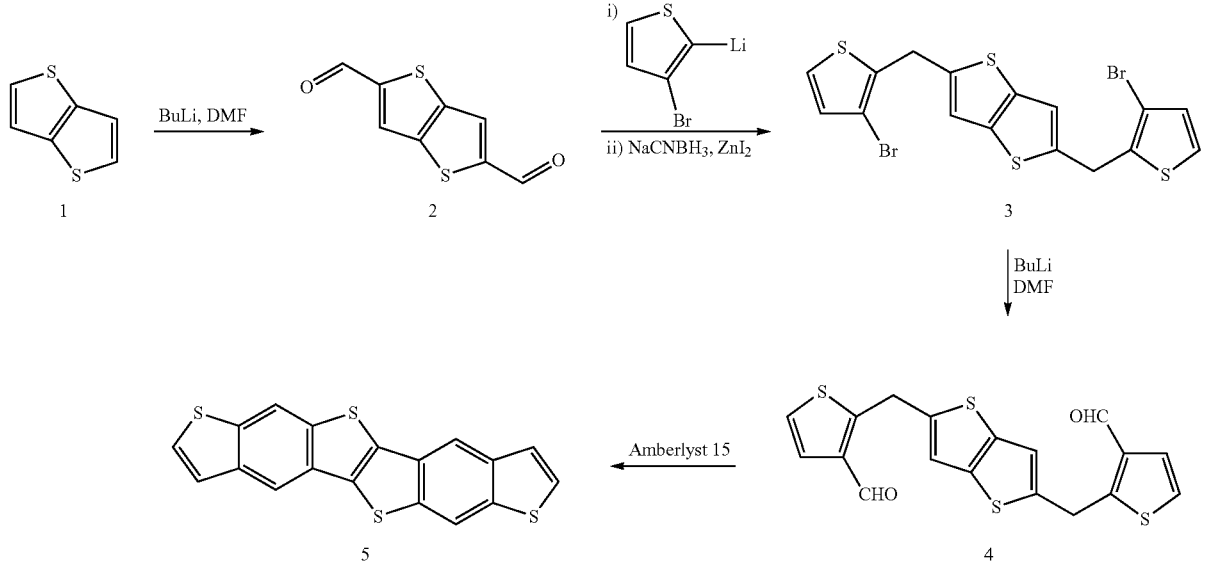

(1) Synthesis of Compound 2

Thienothiophene 1 is synthesized in a method developed by Iddon and the like (Reference: Lance S. Fuller, Brian Iddon, Kevin A. Smith J. Chem. Soc., Perkin Trans. 1, 1997, 3465-3470). Thienothiophene (3.35 g, 24 mmol) is dissolved in 50 mL of dry ether, and the solution is added in a dropwise fashion to 100 mL of a dry ether solution including butyl lithium (2.5 M in 21 mL of a hexane solution) cooled down to 0° C., and the mixture is slowly heated up to room temperature and stirred for 2 hours. Subsequently, dimethyl formamide (DMF; 4.6 mL) is added in a dropwise fashion to the opaque solution, and the obtained mixture is stirred overnight. Then, 50 mL of an ammonium chloride-saturated solution is added thereto, and a precipitate therein is filtered and several times washed with water and ether to obtain desired Compound 2 (A yield: 75%).

$^1$NMR (CDCl$_3$) d 10.1 (s, 2H), 8.05 (s, 2H).

(2) Synthesis of Compound 3

2,3-dibromothiophene (2.42 g, 10 mmole) is dissolved in 100 mL of a mixed solution of ether and THF in a ratio of 5:1, and the obtained solution is cooled down to −78° C. Subsequently, butyl lithium (11 mmole) is slowly added thereto in a dropwise fashion, and the obtained mixture is stirred for 30 minutes. This solution is slowly added in a dropwise fashion to the other solution that Compound 2 (0.99 g, 5 mmole) is dissolved in 100 mL of THF (−78° C.), and the obtained mixture is heated up to room temperature. Then, 100 mL of an ammonium chloride-saturated solution is added thereto to complete a reaction, 200 mL of ether is added thereto to separate an organic layer. The separated organic layer is washed with brine, dried with MgSO$_4$, and concentrated to obtain yellow oil. This material is purified with a silica chromatography (hexane:ethyl acetate=5:1) to obtain a desired diol compound.

$^1$NMR (CDCl$_3$) d 7.32 (d, 2H), 7.18 (s, 2H), 6.97 (dd, 2H), 6.42 (d, 2H), 2.76 (d, 2H).

The diol compound (1.4 g, 2.7 mmole) is dissolved in 150 mL of dichloromethane, and ZnI$_2$ (2.75 g, 8.6 mmole) and NaCNBH$_3$ (2.4 g, 37.66 mmole) are slowly added thereto. The mixture is stirred at room temperature for 24 hours and passed through a Celite pad. A filtrate therefrom is respectively washed with an ammonium chloride-saturated solution and water, dried with MgSO$_4$, and concentrated under a reduced pressure to obtain yellow oil. This material is purified with a silica chromatography to obtain desired Compound 3 (A yield: 80%).

$^1$NMR (CDCl$_3$) d 7.17 (d, 2H), 6.98 (s, 2H), 6.94 (d, 2H), 4.34 (s, 4H)

(3) Synthesis of Compound 4

A THF (5 mL) solution prepared by dissolving Compound 3 (385 mg, 0.79 mmole) is dissolved in 10 mL of a THF solution prepared by dissolving butyl lithium (1.73 mmole) and cooled down to −78° C. is slowly added in a dropwise fashion. The mixture is stirred at −78° C. for about 20 minutes, DMF (150 mL, 1.97 mmole) is added thereto, and the obtained mixture is additionally stirred for about 2 hours. After completing a reaction after pouring water thereinto, 30 mL of ether is added thereto, the obtained mixture is washed with water and brine, and an organic layer therefrom is dried with MgSO$_4$ and concentrated under reduced pressure to obtain colorless oil. This material is purified with a silica chromatography to obtain desired Compound 4 (A yield: 70%).

NMR (CDCl$_3$) d 10.1 (s, 2H), 7.43 (d, 2H), 7.20 (d, 2H), 7.02 (s, 2H), 4.76 (s, 4H).

(4) Synthesis of Compound 5

200 mg of Compound 4 is dissolved in 1 mL of toluene, 300 mg of Amberlyst 15 is added thereto, and water is removed by using a Dean-Stark trap, while the mixture is stirred and refluxed. After 24 hours or so, a beige solid is precipitated. The Amberlyst 15 is precipitated by decreasing the temperature down to room temperature and after skimming a floating material, filtered to obtain Compound 5 as a light yellow solid (fluorescent light blue appears) (A yield: 60%). Compound 5 is purified using a sublimation method under high vacuum (<10$^{-4}$ torr) (m.p. 423).

Comparative Synthesis Example 2

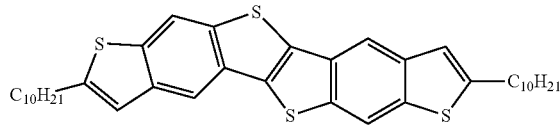

[Chemical Formula X]

A compound represented by Chemical Formula X is obtained by referring to Paragraphs [0061] to [0091] of U.S. Pat. No. 7,816,673 (U.S. Pat. No. 7,816,673 B2, 2010 Oct. 19).

Comparative Synthesis Example 3

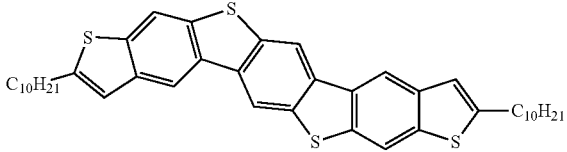

[Chemical Formula Y]

A compound represented by Chemical Formula Y is obtained by referring to Paragraphs [0113] to [0148] of Korean Patent Laid-Open Publication No. 10-2013-0136938 (2013 Dec. 13).

Thermal Stability of Organic Compound

Thermal stability of the compounds according to Synthesis Example 1 and Comparative Synthesis Examples 1 and 2 is evaluated by measuring a thermal degradation temperature. The thermal degradation temperature (T$_d$) is a temperature where a compound starts to be degraded and thus does not maintain its original molecule structure but transformed. In general, since atoms in a molecule including a compound are evaporated and disappear at the thermal degradation temperature or higher, the thermal degradation temperature may be evaluated as a temperature where an initial weight of the compound starts to decrease. Herein, the thermal degradation temperature is measured in a thermal gravimetric analysis (TGA) method.

Figure 2:
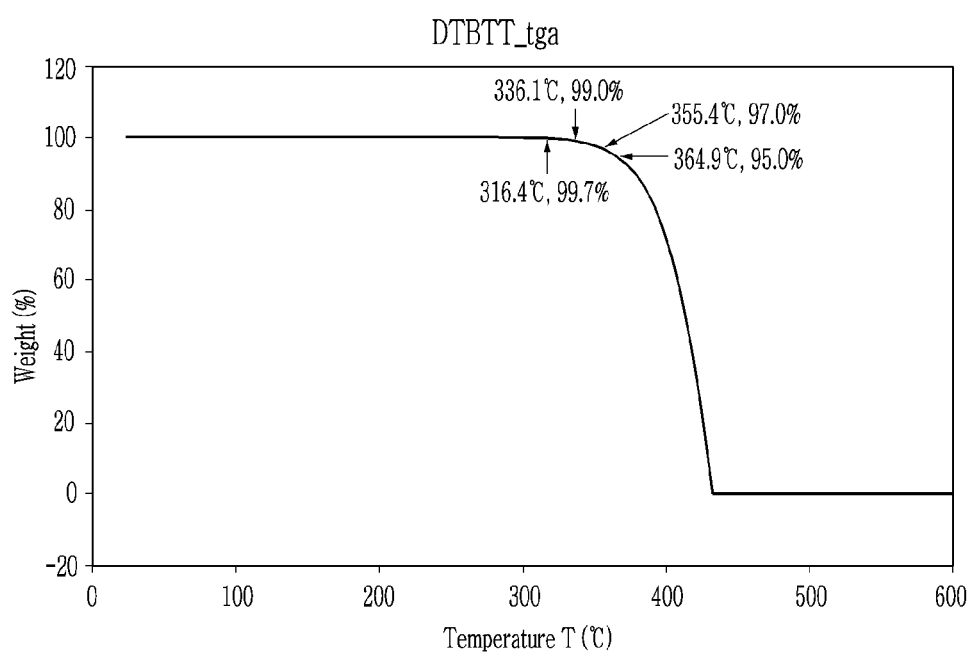
FIG. 2 is a graph showing a thermal gravimetric analysis (TGA) of the compound obtained according to Comparative Synthesis Example 1.
Figure 3:
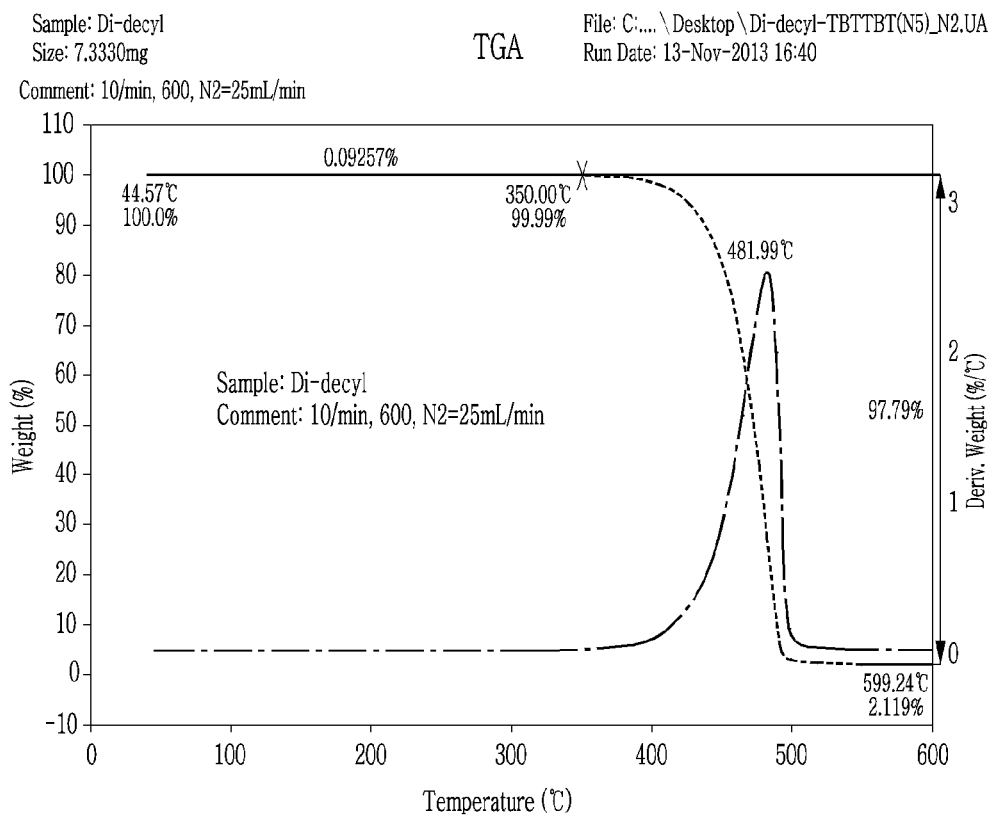
FIG. 3 is a graph showing a TGA of the compound obtained according to Comparative Synthesis Example 2.
Figure 4:
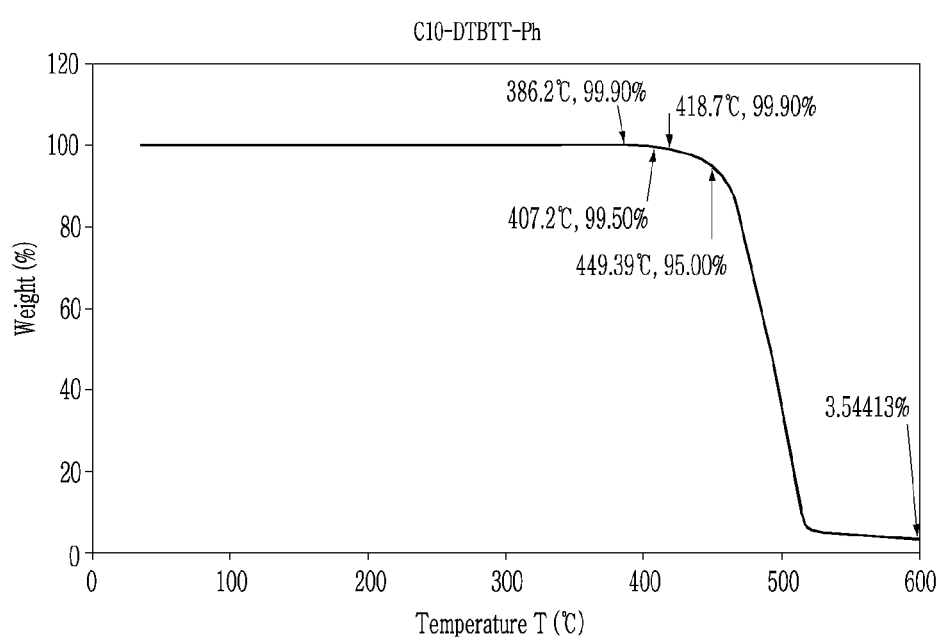
FIG. 4 is a graph showing a TGA of the compound obtained according to Synthesis Example 1.

FIG. 2 is a graph showing a thermal gravimetric analysis (TGA) of the compound obtained according to Comparative Synthesis Example 1, FIG. 3 is a graph showing a TGA of the compound obtained according to Comparative Synthesis Example 2, and FIG. 4 is a graph showing a TGA of the compound obtained according to Synthesis Example 1.

Referring to FIGS. 2 to 4, a degradation temperature where the compound of Comparative Synthesis Example 1 loses 1 wt % is about 336° C., that of the compound of Comparative Synthesis Example 2 is about 350° C., and that of the compound of Synthesis Example 1 is about 386° C. Accordingly, the compound of Synthesis Example 1 shows excellent thermal stability compared with the compounds of Comparative Synthesis Examples 1 and 2.

Liquid Crystal Characteristics of Organic Compound

Liquid crystal characteristics of the compounds according to Synthesis Example 1 and Comparative Synthesis Examples 1 to 3 are examined by using differential scanning calorimetry (DSC).

Figure 5:
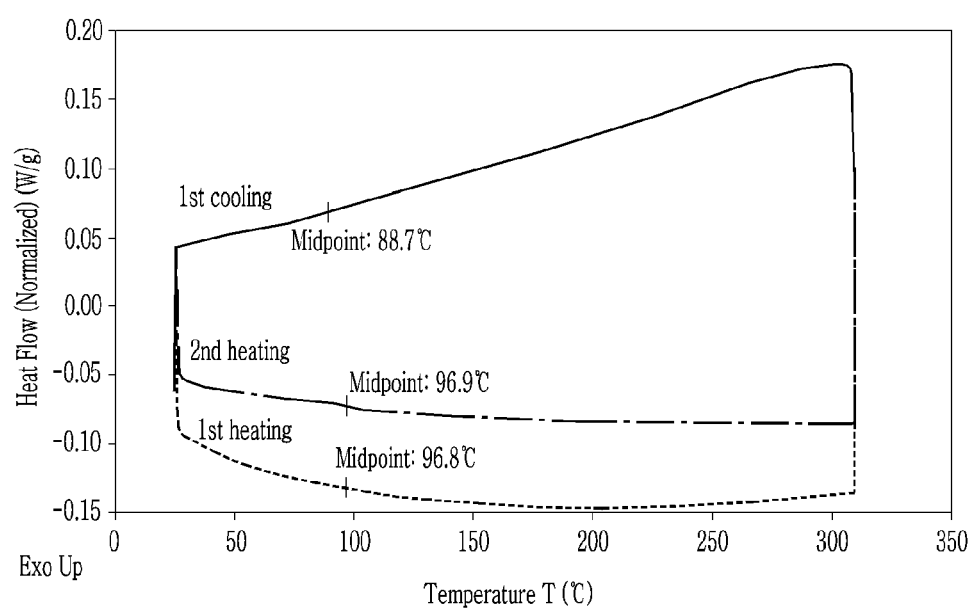
FIG. 5 is a graph showing differential scanning calorimetry (DSC) of the compound obtained according to Comparative Synthesis Example 1.
Figure 6:
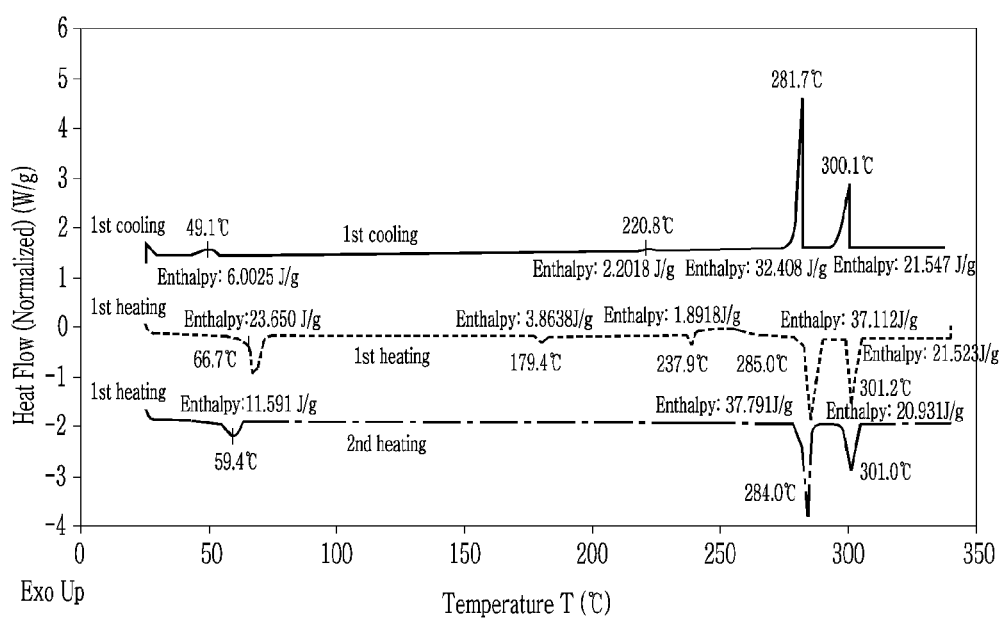
FIG. 6 is a graph showing DSC of the compound obtained according to Comparative Synthesis Example 2.
Figure 7:
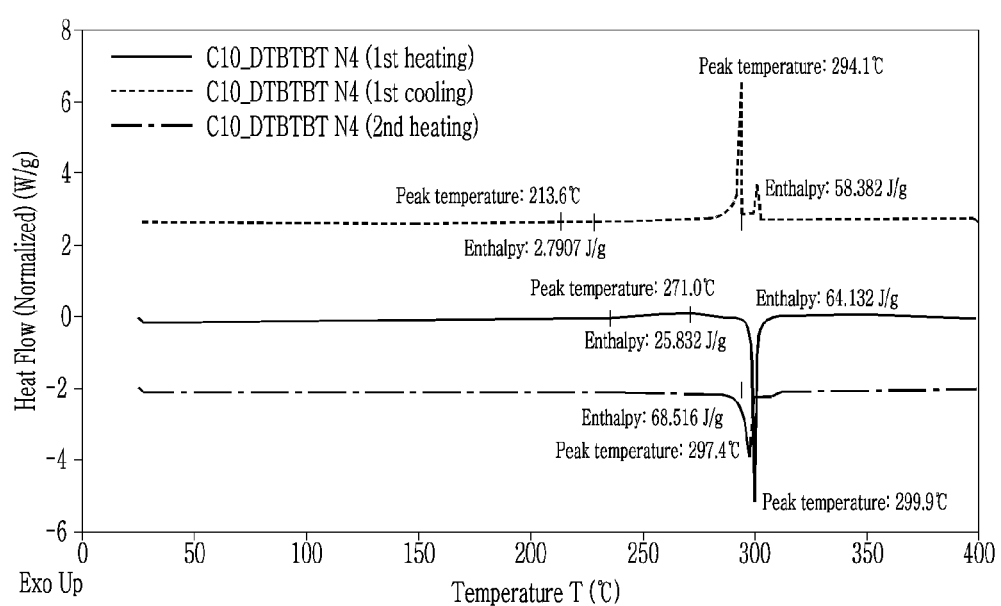
FIG. 7 is a graph showing DSC of the compound obtained according to Comparative Synthesis Example 3.
Figure 8:
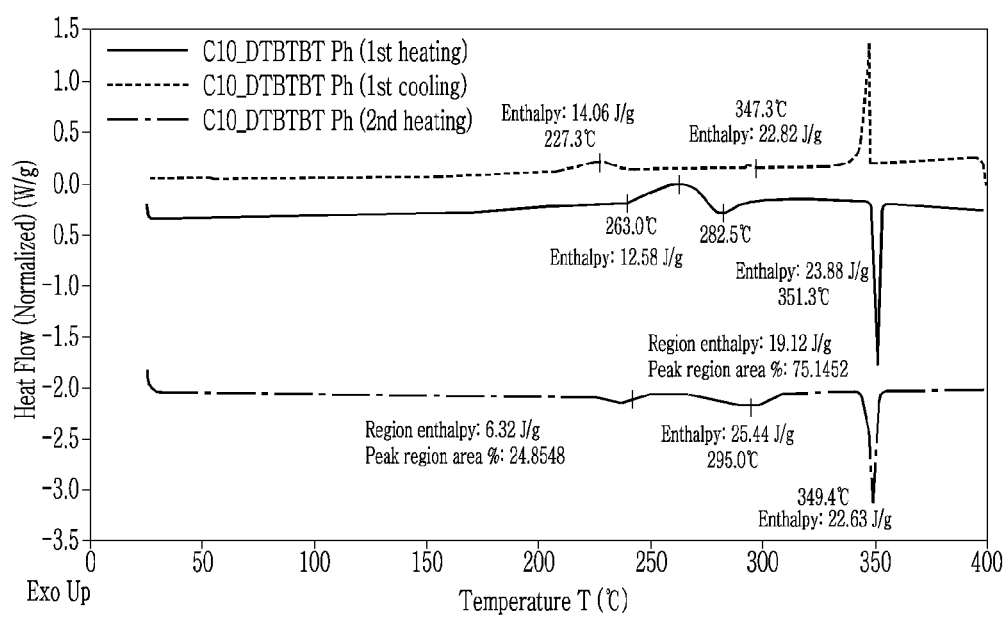
FIG. 8 is a graph showing DSC of the compound obtained according to Synthesis Example 1.
Figure 9:
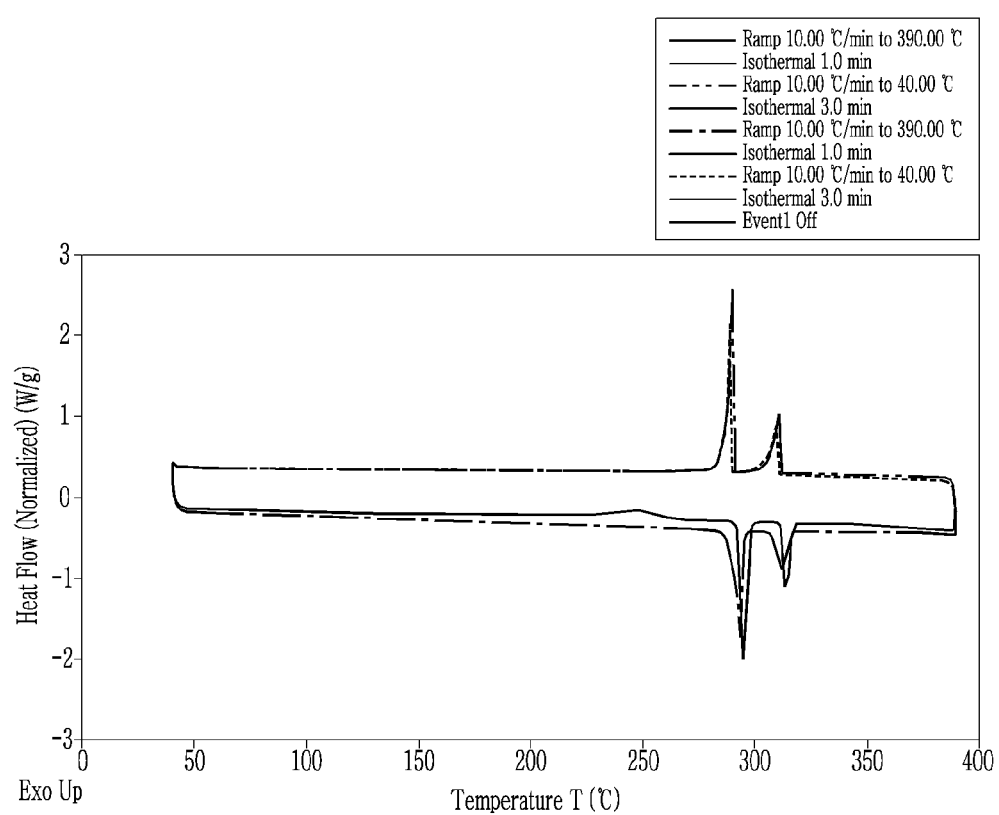
FIG. 9 is a graph showing DSC of the compound obtained according to Synthesis Example 2.
Figure 10:
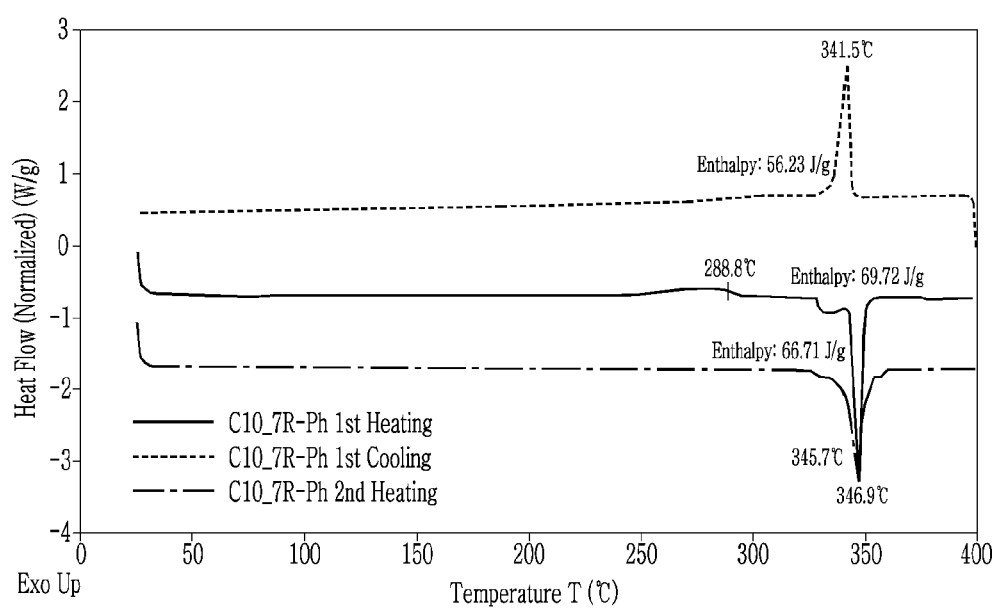
FIG. 10 is a graph showing DSC of the compound obtained according to Synthesis Example 3.
Figure 11:
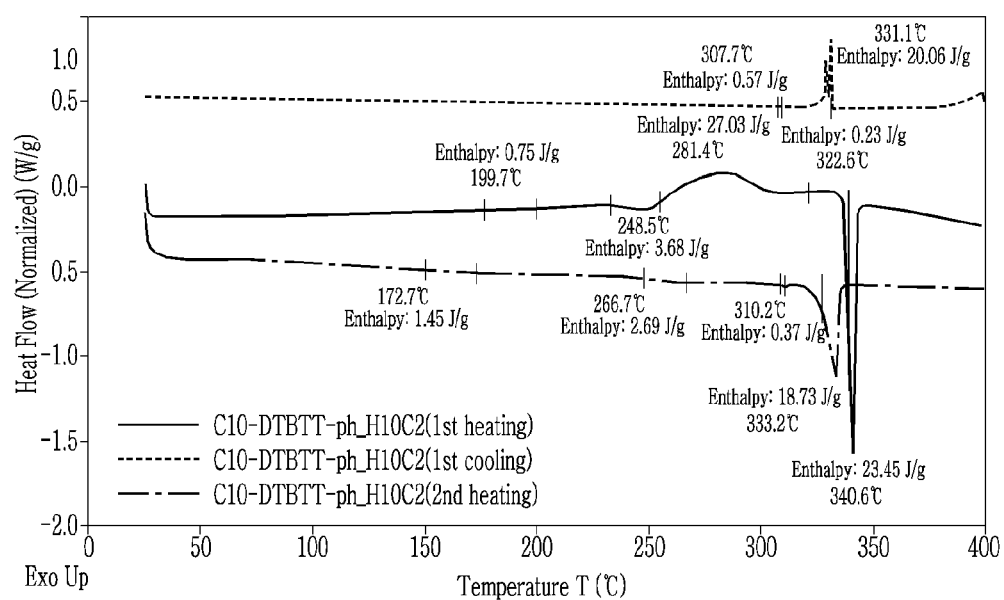
FIG. 11 is a graph showing DSC of the compound obtained according to Synthesis Example 4.
Figure 12:
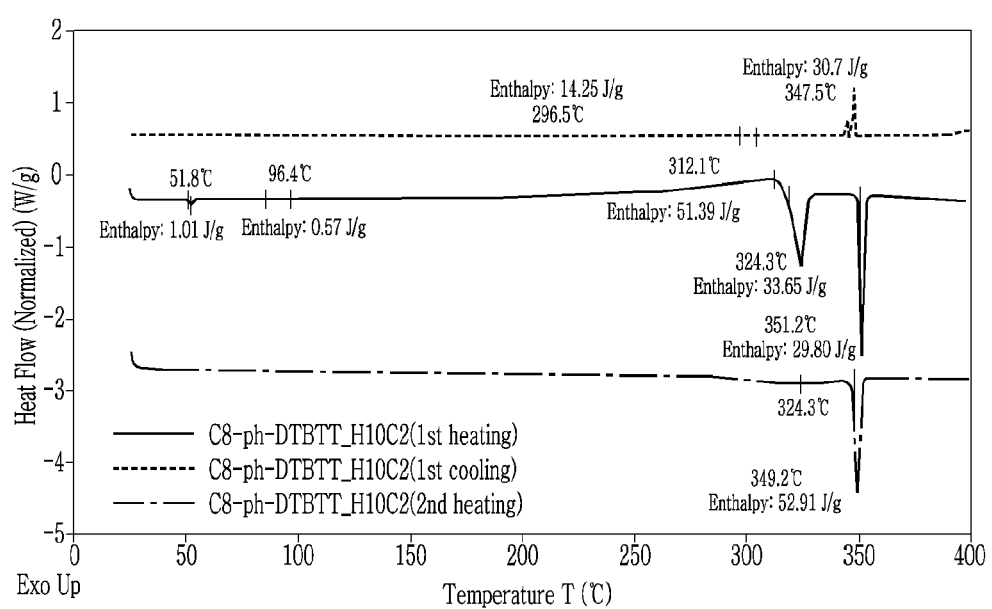
FIG. 12 is a graph showing DSC of the compound obtained according to Synthesis Example 5.

FIGS. 5 to 7 are graphs showing differential scanning calorimetry (DSC) of each compound according to Comparative Synthesis Examples 1 to 3, respectively, and FIGS. 8 to 12 are graphs showing differential scanning calorimetry (DSC) of each compound according to Synthesis Examples 1 to 5, respectively.

Referring to FIGS. 5 to 12, the compound of Comparative Synthesis Example 1 shows no liquid crystalline, the compounds of Comparative Synthesis Examples 2 and 3 show nematic liquid crystalline, the compounds of Synthesis Examples 1 to 5 show smectic liquid crystalline as well as nematic liquid crystalline (2D structure).

Example 1

Manufacture of Organic Thin Film Transistor (OTFT)

First, a gate electrode is formed on a cleaned glass substrate by depositing chromium to be 1000 Å thick in a sputtering method, and an insulation layer is formed by depositing $SiO_2$ to be 3000 Å thick in a CVD method. Then, a source electrode and a drain electrode are formed by depositing Au to be 700 Å thick in a sputtering method. The glass substrate is washed for 10 minutes by using isopropyl alcohol and dried before coating an organic compound. In addition, the surface of $SiO_2$ used as the insulation layer is treated with $UV/O_3$ for 30 minutes before modified. Then, the substrate is dipped in an octyltrichlorosilane solution diluted in n-hexane at a concentration of 10 mM for 30 minutes and then, washed with hexane and ethanol and then dried, and the organic compound of Synthesis Example 1 is deposited at 185° C. at a rate of 1 Å/s to form a 330 Å-thick active layer and annealed at 225° C. for 2 hours to manufacture an organic thin film transistor.

Examples 2 to 5 and Comparative Examples 1 to 3

Each organic thin film transistor is manufactured according to the same method as Example 1 except for respectively using the organic compounds of Synthesis Examples 2 to 5 and Comparative Synthesis Examples 1 to 2 instead of the organic compound of Synthesis Example 1.

Electrical Characteristics Evaluation

Current transport characteristic curves of the organic thin film transistors (OTFT) of Examples 1 to 5 and Comparative Examples 1 to 3 are measured by using Semiconductor Characterization System (4200-SCS) made by Keithley Instruments Company. Charge mobility of the organic thin film transistor according to Example 1 is shown in Table 1.

TABLE 1

| Devices | Charge mobility (cm²/Vs) | $I_{on}$ (On current, A) | $I_{on}/I_{off}$ |
|---|---|---|---|
| Example 1 | 11.6 | $6.2 \times 10^{-4}$ | $10^6$ |
| Comparative Example 1 | 7 | $2.0 \times 10^{-4}$ | $10^6$ |
| Comparative Example 2 | 7 | $2.5 \times 10^{-4}$ | $10^6$ |

The charge mobility of Table 1, is obtained from a slope of a graph of $(ISD)^{1/2}$ and $V_G$ parameters obtained from Equation 1 in a saturation region.

$$I_{SD} = \frac{WC_0}{2L}\mu(V_G - V_T)^2 \quad \text{[Equation 1]}$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In Equation 1, ISD refers to a source-drain current, μ or $\mu_{FET}$ refers to charge mobility, Co refers to oxide layer capacitance, W is a channel width, L is a channel length, $V_G$ is a gate voltage, and $V_T$ is a threshold voltage.

Current on/off ratio ($I_{on}/I_{off}$) is a ratio of an on-state maximum current value ($I_{on}$) with respect to an off-state minimum current value ($I_{off}$).

Referring to the results of Table 1, the organic thin film transistor of Example 1 shows excellent electrical characteristics compared with the organic thin film transistors according to Comparative Examples 1 and 2.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. An organic compound represented by Chemical Formula 1A,

[Chemical Formula 1A]

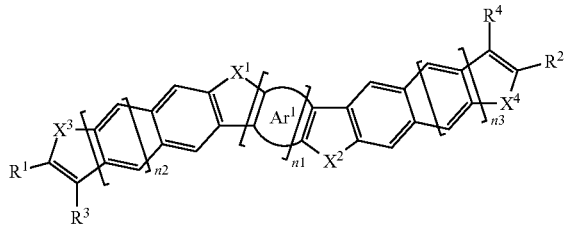

wherein, in Chemical Formula 1A,
one of benzene, naphthalene, or anthracene,
$X^1$ to $X^4$ are independently one of S,
n1, n2, and n3 are independently 0 or 1,
$R^1$ to $R^4$ are independently one of hydrogen, a halogen atom, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are different structures from each other or $R^3$ and $R^4$ are different structures from each other, wherein the organic compound exhibits a smectic phase in a temperature-increasing region of about 300° C. of a differential scanning calorimetry (DSC) analysis.

2. The organic compound of claim 1, wherein n1 is 0 and n2=n3, or n1 is 1, n2=0, and n3=0.

3. The organic compound of claim 1, wherein one of $R^1$ and $R^2$ is one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^1$ and $R^2$ is one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ are independently one of hydrogen or a halogen atom; or one of $R^3$ and $R^4$ is one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, another of $R^3$ and $R^4$ is one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are independently one of hydrogen or a halogen atom.

4. The organic compound of claim 3, wherein $R^2$ is one of a fluoro-substituted C6 to C30 aryl group, a fluoro-substituted C2 to C30 heteroaryl group, a fluoro-substituted C7 to C30 alkylaryl group, a fluoro-substituted C2 to C30 alkylheteroaryl group, a fluoro-substituted C5 to C30 cycloalkyl group, a fluoro-substituted C2 to C30 heterocycloalkyl group, or a combination thereof.

5. The organic compound of claim 3, wherein $R^2$ is one of a substituted or unsubstituted pentagonal ring, a substituted or unsubstituted hexagonal ring, or a combination thereof.

6. The organic compound of claim 5, wherein $R^2$ is one of a heterocyclic group represented by Chemical Formula 2A or 2B, a substituted or unsubstituted alkylaryl group represented by Chemical Formula 2C, or a combination thereof:

[Chemical Formula 2A]

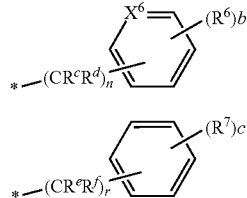

[Chemical Formula 2B]

[Chemical Formula 2C]

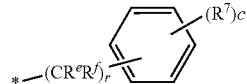

wherein, in Chemical Formulae 2A, 2B, and 2C, $X^5$ is one of O, S, Se, Te, or $NR^{aa}$, wherein $R^{aa}$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, $X^6$ is N, $R^5$, $R^6$, and $R^7$ are independently one of a halogen atom, a hydroxy group, a substituted or unsubstituted C1 to C30 alkyl group, a substituted or unsubstituted C1 to C30 alkoxy group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a combination thereof, a is an integer of 0 to 3, b is an integer of 0 to 4, c is an integer of 0 to 4, $R^a$ and $R^b$ are independently one of hydrogen or a C1 to C6 alkyl group, m is 0 to 20, and when m is 2 or more, —($CR^aR^b$)— is optionally replaced by one of —O—, —C(=O)—, —OC(=O)O—, or —C(=O)O—, $R^c$ and $R^d$ are independently one of hydrogen or a C1 to C6 alkyl group, n is 0 to 20, and when n is 2 or more, —($CR^eR^d$)— is optionally replaced by one of —O—, —C(=O)—, —OC(=O)O—, or —C(=O)O—, $R^e$ and $R^f$ are independently one of hydrogen or a C1 to C6 alkyl group, r is 0 to 20, when r is 2 or more, —($CR^eR^f$)— is optionally replaced by one of —O—, —C(=O)—, —OC(=O)O—, or —C(=O)O—, and

* is a linking point.

7. The organic compound of claim 1, wherein one of $R^1$ and $R^2$ is one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, an other of $R^1$ and $R^2$ is one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^3$ and $R^4$ are independently one of hydrogen or a halogen atom; or one of $R^3$ and $R^4$ is one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, an other of $R^3$ and $R^4$ is one of a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and $R^1$ and $R^2$ are independently one of hydrogen or a halogen atom.

8. The organic compound of claim 7, wherein
$R^2$ is one of a fluoro-substituted C6 to C30 aryl group, a fluoro-substituted C2 to C30 heteroaryl group, a fluoro-substituted C7 to C30 alkylaryl group, a fluoro-substituted C2 to C30 alkytheteroaryl group, a fluoro-substituted C5 to C30 cycloalkyl group, a fluoro-substituted C2 to C30 heterocycloalkyl group, or combination thereof.

9. The organic compound of claim 7, wherein
$R^2$ is one of a substituted or unsubstituted pentagonal ring, a substituted or unsubstituted hexagonal ring, or a combination thereof.

10. The organic compound of claim 9, wherein $R^2$ is one of a substituted or unsubstituted phenyl group, a heterocyclic group represented by Chemical Formula 2A or 2B, or a combination thereof:

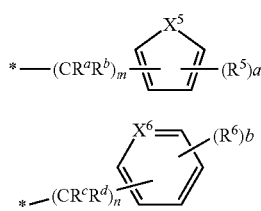

[Chemical Formula 2A]

[Chemical Formula 2B]

wherein, in Chemical Formulae 2A, and 2B,
$X^5$ is one of O, S, Se, Te, or $NR^{aa}$, wherein $R^{aa}$ is one of hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a hydroxy group, a halogen atom, or a combination thereof, $X^6$ is N, $R^5$, and $R^6$ are independently one of a halogen atom, a hydroxy group, a substituted or unsubstituted C1 to C30 alkyl group, a substituted or unsubstituted C1 to C30 alkoxy group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, or a substituted or unsubstituted C2 to C30 alkynyl group, or a combination thereof, a is an integer of 0 to 3,
b is an integer of 0 to 4,
$R^a$ and $R^b$ are independently one of hydrogen or a C1 to C6 alkyl group, m is 0 to 20, and when m is 2 or more, —$(CR^aR^b)$— is optionally replaced by one of —O—, —C(=O)—, —OC(=O)O—, or —C(=O)O—,
$R^c$ and $R^d$ are independently one of hydrogen or a C1 to C6 alkyl group, n is 0 to 20, and when n is 2 or more, —$(CR^cR^d)$— is optionally replaced by one of —O—, —C(=O)—, —OC(=O)O—, or —C(=O)O—, and
* is a linking point.

11. The organic compound of claim 1, wherein
one of $R^1$ and $R^2$ is one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^1$ and $R^2$ is one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^3$ and $R^4$ are independently one of a hydrogen or a halogen atom; or one of $R^3$ and $R^4$ is one of a substituted or unsubstituted linear C1 to C30 alkyl group, a substituted or unsubstituted linear C2 to C30 alkenyl group, a substituted or unsubstituted linear C2 to C30 alkynyl group, or a combination thereof, an other of $R^3$ and $R^4$ is one of a substituted or unsubstituted branched C3 to C30 alkyl group, a substituted or unsubstituted branched C4 to C30 alkenyl group, a substituted or unsubstituted branched C4 to C30 alkynyl group, or a combination thereof, and $R^1$ and $R^2$ are independently one of hydrogen or a halogen atom.

12. The organic compound of claim 1, wherein
n1 is 1, and
$Ar^1$ is benzene.

13. The organic compound of claim 1, wherein a molecular weight of the organic compound is in a range of about 300 to about 5,000.

14. The organic compound of claim 1, wherein
$R^1$ and $R^2$ have different structures from each other and $R^3$ and $R^4$ are independently one of hydrogen or a halogen atom, or $R^3$ and $R^4$ have different structures form each other and $R^1$ and $R^2$ are independently one of hydrogen or a halogen atom.

15. An organic thin film comprising:
the organic compound of claim 1.

16. An organic thin film transistor, comprising
the organic compound of claim 1;
a gate electrode,
an organic semiconductor overlapping with the gate electrode, and
a source electrode and a drain electrode electrically connected to the organic semiconductor, wherein
the organic semiconductor includes the organic compound.

17. An electronic device comprising:
the organic thin film transistor of claim 16.

18. The electronic device of claim 17, wherein the electronic device includes one of a solar cell, a liquid crystal display (LCD), an organic light emitting diode device, an electrophoretic device, an organic photoelectric device, an organic sensor, or a combination thereof.

19. An electronic device comprising:
the organic thin film of claim 15.

20. An organic semiconductor, comprising:
an organic compound represented by Chemical Formula 1A

[Chemical Formula 1A]

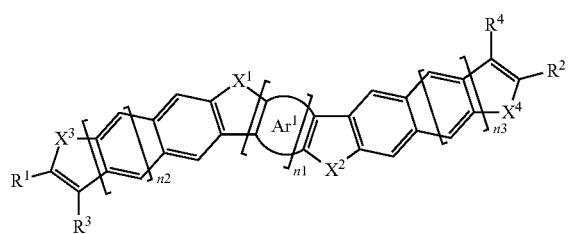

wherein, in Chemical Formula 1A,
$Ar^1$ is one of benzene, naphthalene, or anthracene,
$X^1$ to $X^4$ are independently one of S,
n1 is 1,
n2 and n3 are 0 or 1,
n2=n3,
$R^1$ to $R^4$ are independently one of hydrogen, a halogen atom, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C6 to C30 aryl group, a substituted or unsubstituted C2 to C30 heteroaryl group, a substituted or unsubstituted C7 to C30 alkylaryl group, a substituted or unsubstituted C2 to C30 alkylheteroaryl group, a substituted or unsubstituted C7 to C30 arylheteroalkyl group, a substituted or unsubstituted C5 to C30 cycloalkyl group, a substituted or unsubstituted C2 to C30 heterocycloalkyl group, or a combination thereof, and
$R^1$ and $R^2$ are different structures from each other or $R^3$ and $R^4$ are different structures from each other,
wherein the organic compound exhibits a smectic phase in a temperature-increasing region of about 300° C. of a differential scanning calorimetry (DSC) analysis.

21. An organic thin film transistor, comprising
an organic semiconductor layer including the organic semiconductor of claim 20;
a gate electrode facing the organic semiconductor layer;
a gate insulating layer between the organic semiconductor layer and the gate electrode, the gate insulating layer connected to the gate electrode and the organic semiconductor layer; and
a source electrode and a drain electrode spaced apart from each other and spaced apart from the gate electrode, the source electrode and the drain electrode being electrically connected to the organic semiconductor layer.

22. An electronic device comprising:
the organic thin film transistor of claim 21, wherein the organic semiconductor layer is on the gate electrode.

* * * * *